(12) United States Patent
Kerem et al.

(10) Patent No.: US 10,428,328 B2
(45) Date of Patent: Oct. 1, 2019

(54) RESTORATION OF THE CFTR FUNCTION BY SPLICING MODULATION

(71) Applicant: Yissum Research Development Company of the Hebrew University of Jerusalem Ltd., Jerusalem (IL)

(72) Inventors: Batsheva Kerem, Mevaseret Zion (IL); Michal Tur Sinai, Mevaseret Zion (IL); Loren Price, Wembley (AU); Stephen Donald Wilton, Applecross (AU); Sue Fletcher, Bayswater (AU)

(73) Assignee: YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 14/667,285

(22) Filed: Mar. 24, 2015

(65) Prior Publication Data

US 2015/0211010 A1   Jul. 30, 2015

Related U.S. Application Data

(63) Continuation of application No. PCT/IL2013/050789, filed on Sep. 17, 2013.
(Continued)

(51) Int. Cl.
*C12N 15/11* (2006.01)
*C12N 15/113* (2010.01)
(Continued)

(52) U.S. Cl.
CPC ........ *C12N 15/113* (2013.01); *A61K 31/7105* (2013.01); *A61K 45/06* (2013.01);
(Continued)

(58) Field of Classification Search
CPC .............. C12N 15/113; C12N 15/1138; C12N 2310/11; C12N 2310/315; C12N 2320/31;
(Continued)

(56) References Cited

U.S. PATENT DOCUMENTS 5,580,969 A    12/1996 Hoke
7,176,303 B2   2/2007 Freier et al.
(Continued)

FOREIGN PATENT DOCUMENTS

EP   0 636 137 B1   3/1997
WO   0009734 A1    2/2000
(Continued)

OTHER PUBLICATIONS

Frédéric Becq (Drugs, 2010 vol. 70(3):241-259).*
(Continued)

*Primary Examiner* — Terra C Gibbs
(74) *Attorney, Agent, or Firm* — The Roy Gross Law Firm, LLC; Roy Gross

(57) ABSTRACT

Oligonucleotides capable of binding to and modulating the splicing of the pre-mRNA of the CFTR gene, compositions including the oligonucleotides, kits including the compositions, and uses thereof. Compositions of oligonucleotides useful in methods for suppressing exon 10 skipping optionally in combination with additional CFTR therapeutics.

9 Claims, 9 Drawing Sheets

Specification includes a Sequence Listing.

Related U.S. Application Data

(60) Provisional application No. 61/704,859, filed on Sep. 24, 2012.

(51) Int. Cl.
    *A61K 48/00* (2006.01)
    *C07H 21/02* (2006.01)
    *C07H 21/04* (2006.01)
    *A61K 31/7105* (2006.01)
    *A61K 45/06* (2006.01)

(52) U.S. Cl.
    CPC ...... *C12N 15/1138* (2013.01); *C12N 2310/11* (2013.01); *C12N 2310/315* (2013.01); *C12N 2310/321* (2013.01); *C12N 2320/31* (2013.01); *C12N 2320/33* (2013.01)

(58) Field of Classification Search
    CPC ............ C12N 2320/33; A61K 31/7088; A61K 31/7105; A61P 11/00
    USPC .......................................................... 514/44
    See application file for complete search history.

(56) References Cited

U.S. PATENT DOCUMENTS

| | | |
|---|---|---|
| 8,501,703 B2 | 8/2013 | Bennett et al. |
| 9,157,081 B2 | 10/2015 | Bennett et al. |

FOREIGN PATENT DOCUMENTS

| | | | |
|---|---|---|---|
| WO | WO 2003/074737 A1 | * | 12/2003 |
| WO | 2008/074023 A2 | | 6/2008 |

OTHER PUBLICATIONS

GenBank Accession No. NG_016465.4, downloaded from https://www.ncbi.nlm.nih.gov/nuccore/NG_016465.4 on Apr. 15, 2018.*
Flume et al. (Chest, 2012 vol. 142:718-724, published online Mar. 1, 2012).*
Chu et al., (1993) Genetic basis of variable exon 9 skipping in cystic fibrosis transmembrane conductance regulator mRNA. Nat Genet 3(2): 151-6.
Cirak et al., (2011) Exon skipping and dystrophin restoration in patients with Duchenne muscular dystrophy after systemic phosphorodiamidate morpholino oligomer treatment: an open-label, phase 2, dose-escalation study. Lancet 378(9791): 595-605.
Cutting et al., (1990) A cluster of cystic fibrosis mutations in the first nucleotide-binding fold of the cystic fibrosis conductance regulator protein. Nature 346(6282): 366-9.
Dhir and Buratti (2010) Alternative splicing: role of pseudoexons in human disease and potential therapeutic strategies. FEBS J 277(4): 841-55.
Friedman et al., (1999) Correction of aberrant splicing of the cystic fibrosis transmembrane conductance regulator (CFTR) gene by antisense oligonucleotides. J Biol Chem 274(51): 36193-9.
Gebski et al., (2003) Morpholino antisense oligonucleotide induced dystrophin exon 23 skipping in mdx mouse muscle. Hum Mol Genet 12(15): 1801-11.
Goemans et al., (2011) Systemic administration of PRO051 in Duchenne's muscular dystrophy. N Engl J Med 364(16): 1513-22.
Goyenvalle et al., (2010) Prevention of dystrophic pathology in severely affected dystrophin/utrophin-deficient mice by morpholino-oligomer-mediated exon-skipping. Mol Ther 18(1): 198-205.
Groman et al., (2004) Variation in a repeat sequence determines whether a common variant of the cystic fibrosis transmembrane conductance regulator gene is pathogenic or benign. Am J Hum Genet 74(1): 176-9.
Hammond and Wood (2011) Genetic therapies for RNA mis-splicing diseases. Trends Genet 27(5): 196-205.

Hefferon et al., (2002) Atypical 5' splice sites cause CFTR exon 9 to be vulnerable to skipping. Am J Hum Genet 71(2): 294-303.
Hefferon et al., (2004) A variable dinucleotide repeat in the CFTR gene contributes to phenotype diversity by forming RNA secondary structures that alter splicing. Proc Natl Acad Sci U S A 101(10): 3504-9.
Hua et al., (2010) Antisense correction of SMN2 splicing in the CNS rescues necrosis in a type III SMA mouse model. Genes Dev 24(15): 1634-44.
Kerem et al., (1990) Identification of mutations in regions corresponding to the two putative nucleotide (ATP)-binding folds of the cystic fibrosis gene. Proc Natl Acad Sci U S A 87(21): 8447-51.
Kerem et al., (1997) A missense cystic fibrosis transmembrane conductance regulator mutation with variable phenotype. Pediatrics 100(3): E5.
Kiesewetter et al., (1993) A mutation in CFTR produces different phenotypes depending on chromosomal background. Nat Genet 5(3): 274-8.
Kinali et al., (2009) Local restoration of dystrophin expression with the morpholino oligomer AVI-4658 in Duchenne muscular dystrophy: a single-blind, placebo-controlled, dose-escalation, proof-of-concept study. Lancet Neurol 8(10): 918-28.
King and Sorscher (2000) R-domain interactions with distal regions of CFTR lead to phosphorylation and activation. Biochemistry 39(32): 9868-75.
Liu et al., (2002) Partial correction of endogenous DeltaF508 CFTR in human cystic fibrosis airway epithelia by spliceosome-mediated RNA trans-splicing. Nat Biotechnol 20(1): 47-52.
Lorson et al., (2010) Spinal muscular atrophy: mechanisms and therapeutic strategies. Hum Mol Genet 19(R1): R111-8.
Lu et al., (2011) The status of exon skipping as a therapeutic approach to duchenne muscular dystrophy. Mol Ther 19 (1): 9-15.
Lubamba et al., (2012) Cystic fibrosis: insight into CFTR pathophysiology and pharmacotherapy. Clin Biochem 45(15): 1132-44.
Mann et al., (2001) Antisense-induced exon skipping and synthesis of dystrophin in the mdx mouse. Proc Natl Acad Sci U S A 98(1): 42-7.
Mansfield et al., (2000) Repair of CFTR mRNA by spliceosome-mediated RNA trans-splicing. Gene Ther 7(22): 1885-95.
Mendell et al., (2013) Eteplirsen for the treatment of Duchenne muscular dystrophy. Ann Neurol 74(5): 637-47.
Mitrpant et al., (2009) Rational design of antisense oligomers to induce dystrophin exon skipping. Mol Ther 17(8): 1418-26.
Porensky et al., (2012) A single administration of morpholino antisense oligomer rescues spinal muscular atrophy in mouse. Hum Mol Genet 21(7): 1625-38.
Price et al., (2013) "Silencing a disease modifying mutation for cystic fibrosis using antisense oligonucleotides". The Journal of Gene Medicine 15: 311-40. 8th Australian Gene Therapy Society Meeting, May 8-May 10, 2013. p. 338.
Rogan et al., (2011) Cystic fibrosis transmembrane conductance regulator intracellular processing, trafficking, and opportunities for mutation-specific treatment. Chest 139(6): 1480-90.
Sazani and Kole (2003) Therapeutic potential of antisense oligonucleotides as modulators of alternative splicing. J Clin Invest 112(4): 481-6.
Singh et al., (2009) A short antisense oligonucleotide masking a unique intronic motif prevents skipping of a critical exon in spinal muscular atrophy. RNA Biol 6(3): 341-50.
Tsui (1992) The spectrum of cystic fibrosis mutations. Trends Genet 8(11): 392-8.
van Deutekom et al., (2007) Local dystrophin restoration with antisense oligonucleotide PRO051. N Engl J Med 357 (26): 2677-86.
Williams et al., (2009) Oligonucleotide-mediated survival of motor neuron protein expression in CNS improves phenotype in a mouse model of spinal muscular atrophy. J Neurosci 29(24): 7633-8.
Tsui et al., "The cystic fibrosis gene: a molecular genetic perspective", Cold Spring Harb Perspect Med, vol. 3, No. 2, a009472, 16 pages, (2013).
Buratti et al., (2007) SR protein-mediated inhibition of CFTR exon 9 inclusion: molecular characterization of the intronic splicing silencer. Nucleic acids research, 35(13), 4359-4368.

(56) References Cited

OTHER PUBLICATIONS

El-Seedy et al., (2009) Influence of the duplication of CFTR exon 9 and its flanking sequences on diagnosis of cystic fibrosis mutations. The Journal of Molecular Diagnostics, 11(5), 488-493.

Augarten et al., (1993) Mild cystic fibrosis and normal or borderline sweat test in patients with the 3849 + 10 kb C—>T mutation. Lancet 342(8862): 25-26.

Braasch et al., (2002) Antisense inhibition of gene expression in cells by oligonucleotides incorporating locked nucleic acids: effect of mRNA target sequence and chimera design. Nucleic Acids Res 30(23): 5160-5167.

Chiba-Falek et al., (1998) The molecular basis of disease variability among cystic fibrosis patients carrying the 3849 + 10 kb C—>T mutation. Genomics 53(3): 276-283.

Chu et al., (1993) Genetic basis of variable exon 9 skipping in cystic fibrosis transmembrane conductance regulator mRNA. Nat Genet 3(2): 151-156.

Cutrona et al., (2000) Effects in live cells of a c-myc anti-gene PNA linked to a nuclear localization signal. Nat Biotechnol 18(3): 300-303 abstract.

Debotton et al., (2008) Overcoming the formulation obstacles towards targeted chemotherapy: in vitro and in vivo evaluation of cytotoxic drug loaded immunonanoparticles. J Control Release 127(3): 219-230.

Hagigit et al., (2010) Topical and intravitreous administration of cationic nanoemulsions to deliver antisense oligonucleotides directed towards VEGF KDR receptors to the eye. J Control Release 145(3): 297-305.

Heemskerk et al., (2010) Preclinical PK and PD studies on 2'-O-methyl-phosphorothioate RNA antisense oligonucleotides in the mdx mouse model. Mol Ther 18(6): 1210-1217.

Highsmith et al., (1994) A novel mutation in the cystic fibrosis gene in patients with pulmonary disease but normal sweat chloride concentrations. N Engl J Med 331(15): 974-980.

Kerem et al., (1997) A cystic fibrosis transmembrane conductance regulator splice variant with partial penetrance associated with variable cystic fibrosis presentations. Am J Respir Crit Care Med 155(6): 1914-1920.

Kole et al., (2012) RNA therapeutics: beyond RNA interference and antisense oligonucleotides. Nat Rev Drug Discov 11(2): 125-140.

Larsen et al., (1999) Antisense properties of peptide nucleic acid. Biochim Biophys Acta 1489(1): 159-166.

Linde et al., (2007) Nonsense-mediated mRNA decay affects nonsense transcript levels and governs response of cystic fibrosis patients to gentamicin. J Clin Invest 117(3): 683-692.

Mann et al., (2002) Improved antisense oligonucleotide induced exon skipping in the mdx mouse model of muscular dystrophy. J Gene Med 4(6): 644-654.

Nissim-Rafinia et al., (2002) Splicing regulation as a potential genetic modifier. Trends Genet 18(3): 123-127.

Nissim-Rafinia et al., (2005) The splicing machinery is a genetic modifier of disease severity. Trends Genet 21(9): 480-483.

Nissim-Rafinia et al., (2000) Cellular and viral splicing factors can modify the splicing pattern of CFTR transcripts carrying splicing mutations. Hum Mol Genet 9(12): 1771-1778.

Nissim-Rafinia et al., (2004) Restoration of the cystic fibrosis transmembrane conductance regulator function by splicing modulation. EMBO Rep 5(11): 1071-1077.

Rave-Harel et al., (1997) The molecular basis of partial penetrance of splicing mutations in cystic fibrosis. Am J Hum Genet 60(1): 87-94.

Rowe et al., (2007) Restoration of W1282X CFTR activity by enhanced expression. Am J Respir Cell Mol Biol 37(3): 347-356.

Rowe et al., (2010) DeltaF508 CFTR processing correction and activity in polarized airway and non-airway cell monolayers. Pulm Pharmacol Ther 23(4): 268-278.

Sloane et al., (2012) A pharmacologic approach to acquired cystic fibrosis transmembrane conductance regulator dysfunction in smoking related lung disease. PLoS One 7(6): e39809; 19 pages.

Teixeira et al., (1999) Submicron cationic emulsions as a new delivery system for oligonucleotides. Pharm Res 16 (1): 30-36.

Yin et al., (2008) Effective exon skipping and restoration of dystrophin expression by peptide nucleic acid antisense oligonucleotides in mdx mice. Mol Ther 16(1): 38-45.

Yin et al., (2010) Optimization of peptide nucleic acid antisense oligonucleotides for local and systemic dystrophin splice correction in the mdx mouse. Mol Ther 18(4): 819-827.

Hinrichs et al., (2006) The UCSC Genome Browser Database: update 2006. Nucleic Acids Res 34(Database issue): D590-D598.

\* cited by examiner attgaaatatctgacaaactcatctttattttgatgtgtgtgtgtgtgtttaacagGGATT
TGGGAATTATTTGAGAAAGCAAAACAATAACAATAGAAAAACTT
CTAATGGTGATGACAGCCCTCTTCTTCAGTAATTTCTCACTTCTTGGTACT
CCTGTCCTGAAAGATATTAATTTCAAGATAGAAAGAGGACAGTTGTTGG
CGGTTGCTGGATCCACTGGAGCAGGCAAGgtagttctttgtcttcactattaagaact
taatttggtgtccatgtctcttttttctagtttgtagtgctggaagg (SEQ ID NO:27)

FIGURE 2

(SEQ ID NO:28)

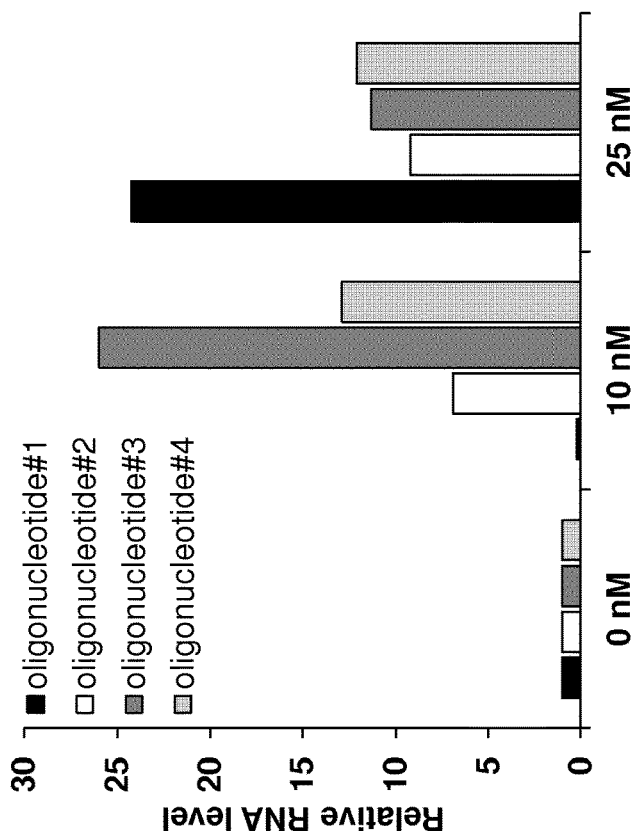
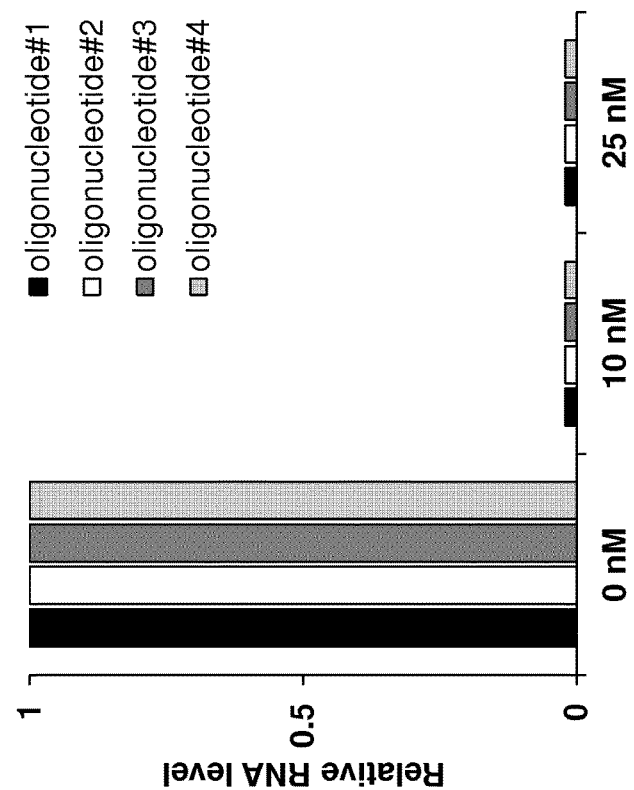
FIGURE 8A
FIGURE 8B

RESTORATION OF THE CFTR FUNCTION BY SPLICING MODULATION

SEQUENCE LISTING

The Sequence Listing submitted in text format (.txt) filed on Jul. 6, 2017, named "SequenceListing.txt", created on Jul. 6, 2017 (30.7 KB), is incorporated herein by reference.

FIELD OF THE INVENTION

The present invention relates to oligonucleotides capable of binding to a Cystic Fibrosis Trans-membrane conductance Regulator (CFTR) pre-mRNA, thereby modulating its splicing. In particular, the present invention provides oligonucleotides and compositions thereof useful in methods for suppressing exon 10 skipping, optionally in combination with additional CFTR splicing modulators or other Cystic Fibrosis therapeutics.

BACKGROUND OF THE INVENTION

Cystic fibrosis (CF) is a common, severe autosomal recessive disease caused by mutations in the CFTR gene. The CFTR gene encodes for a chloride channel responsible for chloride transport in epithelial cells. The major manifestations of CF are in the lungs, with more than 90% mortality related to the respiratory disease. The disease in the respiratory tract is linked to the insufficient CFTR function in the airway epithelium.

As of today, approximately 2000 different mutations disrupting the CFTR functions have been identified worldwide, grouped into five distinct classes based on their effect on the CFTR function (Rogan M. P. et al., 2011). Class I includes mutations that lead to non-functional CFTR (large deletions and stop codon mutations). Class II mutations (including the common F508del) lead to aberrantly folded CFTR protein that is recognized by the cell quality control mechanism and subsequently degraded, resulting in the absence of mature CFTR protein at the apical cell membrane. Class III mutations lead to full-length CFTR protein being incorporated into the cell membrane, but with defective regulation so that no CFTR function is present. These three classes usually lead to a classic CF phenotype with pancreatic insufficiency, although the severity of lung disease is highly variable. CFTR mutations leading to defective chloride conductance are grouped into Class IV. Class V mutations involve transcription dysregulation, resulting in a decreased amount of otherwise normal CFTR. The latter two classes are often associated with a milder phenotype and pancreatic sufficiency. Specifically, CFTR that results from a class IV mutation inserts into the plasma membrane but exhibits reduced single-channel chloride ion conductance because of reduced chloride permeation and open channel probability. R117H, among the most common class IV mutations, occurs at a worldwide frequency approaching 0.5%. The R117H missense mutation causes an arginine-to-histidine substitution at residue 117. R117H-CFTR R domain is normally phosphorylated, and the nucleotide binding domain (NBD) binds adenosine triphosphate (ATP), but channel open time and thus chloride transport are reduced. Additionally, the degree of R117H-CFTR function depends on the length of the polythymidine tract in intron 9 on the same chromosome (which influences splicing efficiency) such that the longer thymidine tracts (9T>7T>5T) produce more functional R117H-CFTR. Clinical disease typically requires the R117H mutation in cis with 5T (Rogan M. P. et al., 2011; Kiesewetter et al., 1993). Found in <1% of patients with CF, class V mutations produce normal plasma membrane CFTR. The quantity, however, is generally reduced as a result of transcriptional dysregulation. Class V mutations frequently influence the splicing machinery and generate both aberrantly and correctly spliced mRNA, the levels of which vary among different patients and even among different organs of the same patients. Ultimately, the splice variants result in a reduced number of functioning CFTR in the plasma membrane (Rogan M. P. et al., 2011).

About 10-15% of CFTR mutations affect the correct splicing of the gene transcripts. Among these are two mutations that are included in the invention: the first is the splicing mutation 3849+10 kb C-to-T which leads to inclusion of an 84 base pair cryptic exon in the mature messenger RNA (mRNA) (denoted "intron 22 cryptic exon inclusion" mutation). The mutation is the 12th most common CFTR mutation in the world, which occurs in hundreds of CF patients worldwide (Kerem et al., 1997; www.genet.sickkids.on.ca/; www.genet.sickkids.on.ca/resource/Table1.html). Correction of said aberrant splicing of the CFTR gene by "anti-sense" oligonucleotides was recently attempted by Friedman et al, 1999.

The second mutation is better described as a sequence variation in the poly $(TG)_n(T)_n$ tract at the acceptor splice site of exon 10 affecting the retention of this exon in the mature mRNA (denoted "exon 10 exclusion" mutation). Importantly, the skipping of the exon results in a non-functional gene transcript, as the exon encodes for the first 21% of the intra-cytoplasmic nucleotide binding fold 1 (NBF1), a critical region for the CFTR function (Cutting et al., 1990; Kerem B. S. et al., 1990). The CFTR gene in many individuals, healthy or CF patients, has an inherent splicing inefficiency of exon 10 due to the non-optimal length of the sequence $(TG)_n(T)_n$ with alleles carrying the $(TG)_{13}(T)_5$ combination generating the highest skipping levels (Chu et al., 2003; Hefferon et al., 2004; Groman et al., 2004).

One of the most promising therapeutic approaches for the treatment of genetic disorders caused by splicing mutations is based on splice-switching "anti-sense" oligonucleotides (AOs) administration. AOs are short synthetic RNA-like molecules chemically modified, which can anneal to motifs predicted to be involved in the pre-mRNA splicing. Their binding to selected sites is expected to mask the targeted region and promote normal splicing. AOs are highly specific for their targets and do not affect any other sequences in the cells. Several types of chemically modified AO molecules are commonly used including: 2'-O-methyl-phosphorothioate (2OMP), phosphorodiamidate morpholino oligomer (PMO), peptide nucleic acids (PNAs), 2-methoxyethyl phosphorothioate (MOE) and alternating locked nucleic acids (LNAs). Two of these are in more common use, 2OMP and PMO.

The AOs modifications maintain their stabilization, improve their target affinity, and provide favorable pharmacokinetic properties and biological stability. It has been conclusively shown that splice-switching AOs can redirect dystrophin pre-mRNA processing in murine models for Duchene Muscular Dystrophy (DMD) so that an exon carrying a premature protein termination signal (nonsense mutation) can be excluded from the mature gene transcript resulting in a shorter but still functional dystrophin isoform (Mann et al., 2001). Progress in dystrophin exon skipping has been rapid, with proof-of-concept studies reported in 2007 (van Deutekom et al., 2007) and 2009 (Kinali et al., 2009), and more recently with the publication of results from systemic administration to patients (Goemans et al., 2011; Cirak et al., 2011; Mendell J. R. et al., 2013). Systemic administration of OMP (5 weekly subcutaneous injections in 12 patients) showed dose-dependent molecular efficacy in patients with DMD (new dystrophin expression in muscle fibers), with a modest improvement in the 6-minute walk test (6MWT) in 8/10 patients which entered a 12 week extension study (Goemans et al., 2011). Systemic administration of PMO (AVI-4658) (12 weekly IV infusions) (Cirak et al., 2001) caused in 7/19 of the patients exon skipping and dystrophin restoration. Moreover, in a recent study published by Mendell J R et al. (Mendell J. R. et al., 2013) the ability of AVI-4658 to induce dystrophin production and to improve distance walk on the 6MWT was evaluated following 48 weeks of weekly IV infusions AVI-4658 restored functional dystrophin expression, causing a mean increase of 47% of dystrophin-positive fibers (change from baseline) together with an improvement in the 6MWT.

In addition to induced exon skipping, AOs can be designed to mask splice-silencing elements that reduce exon recognition and subsequent inclusion in the mature mRNA. Spinal Muscular Atrophy (SMA) is a common autosomal recessive condition (Lorson, Rindt, & Shababi, 2010) caused by the loss of the SMN1 gene together with a C>T variation in SMN2 exon 7, leading to abnormal splicing in which SMN2 exon 7 is skipped, resulting in a non-functional gene product. AOs have been designed to mask nearby flanking SMN2 splice silencer elements to promote synthesis of full-length transcripts (Singh, Shishimorova, Cao, Gangwani, & Singh, 2009; Mitrpant et al., 2009). An intrathecally administration of morpholino oligomer to neonatal mouse pups with severe SMA was highly successful, significantly extending their survival (Porensky et al., 2012).

Different routes of AOs delivery have been examined in animal models and applied in clinical trials, chosen primarily according to the target tissue. For example, 2OMP was administrated to DMD patients (PRO-051) by local intramuscular injection (van Deutekom et al., 2007), and by abdominal subcutaneous injections (Goemans et al., 2011). 2OMP was also administrated to a SMA mouse model by intracerebroventricular injection (Williams et al., 2009; Hua et al., 2010). PMO was administrated to a DMD mouse model by intramuscular injection (Gebski, Mann, Fletcher, & Wilton, 2003), and repeated weakly intraperitoneal injections (Goyenvalle et al., 2010). PMO was also administrated to a SMA mouse model by intracerebroventricular injection (Porensky et al., 2012), and to DMD patients (AVI-4658) by local intramuscular injection (Kinali et al., 2009), or intravenously administration (Cirak et al., 2011; Mendell et al., 2013).

There remains a constant need in the field of Cystic Fibrosis management for novel, potent therapeutics, designed to overcome the numerous mutations in the CFTR gene identified thus far, and restore CFTR function.

SUMMARY OF THE INVENTION

The present invention provides compositions comprising oligonucleotides capable of binding to a CFTR pre-mRNA, thereby modulating splicing and restoring or enhancing the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper skipping of canonical exons and can also avoid improper recognition of intron sequences as exons. As a result of the modulation of splicing, a functional CFTR protein is produced by an otherwise aberrant CFTR allele.

The present invention stems in part from the finding that artificial "anti-sense" polynucleotide molecules are able to target and bind predetermined sequences at the pre-mRNA molecule of the CFTR gene, and that said binding can modulate the splicing of said pre-mRNA molecule into a mature mRNA which is subsequently translated into a functional CFTR protein. The targets within a CFTR pre-mRNA molecule are those discovered to be involved in splicing, either indirectly, by affecting the splicing of adjacent as well as more remote sequences, or directly, by affecting their own splicing.

Thus, in one aspect, the present invention provides a synthetic polynucleotide molecule, comprising a nucleotide sequence comprising a sequence of at least 18 consecutive nucleotide bases, wherein said synthetic polynucleotide molecule is capable of binding to a pre-mRNA transcript of the CFTR gene, and suppressing exon 10 exclusion from the mature CFTR mRNA.

In certain embodiments, the nucleotide sequence comprises at least 18 nucleotides e.g. at least 18 or at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention.

In order to suppress exon 10 exclusion, the synthetic polynucleotide must bind to an exon 10 splicing-silencing-motif found within and/or adjacent to exon 10 of the CFTR gene. Thus, in certain embodiments, the nucleotide sequence is complementary to the nucleotide sequence set forth in SEQ ID NO: 2, or to a fragment thereof. Each possibility represents a separate embodiment of the present invention.

In certain embodiments, said nucleotide sequence comprises a nucleotide sequence set forth in SEQ ID NO: 10 or an active fragment of said nucleotide sequence. Each possibility represents a separate embodiment of the present invention.

The interaction between the synthetic polynucleotide molecules of the present invention and their targets, CFTR pre-mRNA molecules, is primarily a base-base interaction, wherein the nucleotides of the synthetic polynucleotide molecules of the present invention have a base sequence complementary to the base sequence of their CFTR pre-mRNA target(s). It therefore should be understood that the type of backbone used to link the nucleotides of the synthetic polynucleotide molecule of the present invention is secondary, as long as it is known by a man of the art to be appropriate for carrying bases and targeting single stranded DNA and/or RNA molecules. Many such backbones are long known in the art, including the following non-limiting examples of a phosphate-ribose backbone (as in RNA), a phosphate-deoxyribose backbone (as in DNA), a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone (reviewed in Lu et al., 2011), all of which are considered appropriate backbones according to the present invention, and each possibility represents a separate embodiment of the present invention.

Thus, in certain embodiments, the synthetic polynucleotide molecule of the present invention comprises a sequence of at least about 18 consecutive nucleotide bases, wherein each nucleotide comprises a base which is independently selected from adenine, guanine, cytosine, uracil and optionally thymine, attached to each other via one of said backbones.

In another aspect, the present invention provides a pharmaceutical composition comprising a synthetic polynucleotide molecule as described above, and a pharmaceutically acceptable carrier.

In certain embodiments, the pharmaceutical composition is formulated for oral, nasal, aerosol, inhalational, abdominal, subcutaneous, intra-peritoneal or intravenous administration. Each possibility represents a separate embodiment of the present invention.

Being a long-known and well-studied disease, certain drugs and agents are already known in the art for the treatment of Cystic Fibrosis patients. Thus, in certain embodiments, the pharmaceutical composition of the present invention further comprises at least one additional anti-Cystic-Fibrosis agent.

In certain such embodiments, the additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In a more specific such embodiment, said CFTR potentiator is N-(2,4-Di-tert-butyl-5-hydroxyphenyl)-4-oxo-1,4-dihydroquinoline-3-carboxamide (Ivacaftor). In a more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

According to other embodiments, the pharmaceutical composition comprises the synthetic polynucleotide molecule described above capable of suppressing exon 10 exclusion from the mature CFTR mRNA, and a synthetic polynucleotide molecule capable of suppressing intron 22 cryptic exon inclusion in the mature CFTR mRNA.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In another aspect, the present invention provides a synthetic polynucleotide molecule as described above, for use in the modulation of splicing of a CFTR pre-mRNA. Any change in ratio between certain CFTR splicing variants is also considered the result of splicing modulation. Each possibility represents a separate embodiment of the present invention.

Thus, according to certain embodiments, the synthetic polynucleotide molecule described above is for use in reducing the level of an mRNA molecule comprising the nucleotide sequence set forth in SEQ ID NO: 12. In other embodiments, the synthetic polynucleotide molecule described above is for use in increasing the level of an mRNA molecule comprising the nucleotide sequence set forth in SEQ ID NO: 1. In certain embodiments, the synthetic polynucleotide described above comprises the nucleotide sequence set forth in SEQ ID NO: 10, or an active fragment of said nucleotide sequence.

Being a genetic disease, Cystic Fibrosis currently cannot be cured, but its clinical manifestations can be treated by the oligonucleotides of the present invention, for a marked increase and/or improvement in a patient's clinical status and quality of life. Thus, in a further aspect, the present invention provides a method for improving at least one clinical parameter of Cystic Fibrosis in a patient in need thereof, comprising the step of administering a therapeutically effective amount of a synthetic polynucleotide molecule as described above to said patient.

In certain embodiments, the clinical parameter is selected from the group consisting of lung function, time to the first pulmonary exacerbation, a change in weight, a change in height, a change in Body Mass Index (BMI), a change in the concentration of sweat chloride, number and/or duration of pulmonary exacerbations, total number of days of hospitalization for pulmonary exacerbations, or the need for antibiotic therapy for sinopulmonary signs or symptoms. Each possibility represents a separate embodiment of the present invention.

In certain embodiments, the method further comprises administering at least one additional anti-Cystic-Fibrosis agent to said patient.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention. More specific embodiments of said agents are described above.

In certain embodiments, the method comprises administering the synthetic polynucleotide molecule as described above capable of suppressing exon 10 exclusion from the mature CFTR mRNA, and further administering a synthetic polynucleotide molecule capable of suppressing intron 22 cryptic exon inclusion in the mature CFTR mRNA.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, the administration of said synthetic polynucleotide molecule of the present invention and the administration of said at least one additional anti-Cystic-Fibrosis agent are independently oral, nasal, aerosol, inhalational, abdominal, subcutaneous, intra-peritoneal or intravenous administration. Each possibility represents a separate embodiment of the present invention. It should be understood that the selection of an administration route depends on the nature of the therapeutic agent and on the site of its intended effect, and thus certain agents may be administrated via the same or different administration routes.

In a further aspect, the present invention provides a kit comprising a synthetic polynucleotide molecule as described above, and an additional anti-Cystic-Fibrosis agent. In certain embodiments said additional anti-Cystic-Fibrosis agent is selected from the group consisting of a CFTR-splicing-modulating agent, a CFTR potentiator and a CFTR corrector. Each possibility represents a separate embodiment of the present invention. More specific embodiments of said agents are described above.

In other certain embodiments, said kit comprises a synthetic polynucleotide molecule as described above capable of suppressing exon 10 exclusion from the mature CFTR mRNA and a synthetic polynucleotide molecule capable of suppressing intron 22 cryptic exon inclusion in the mature CFTR mRNA.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, said synthetic polynucleotide and said additional anti-Cystic-Fibrosis agent are comprised in one or more, the same or different pharmaceutical compositions. In other certain embodiments, said one or more pharmaceutical compositions are each independently formulated for oral, nasal, aerosol, inhalation, abdominal, subcutaneous, intra-peritoneal or intravenous administration. Each possibility represents a separate embodiment of the present invention.

In a further aspect, the present invention provides a synthetic polynucleotide molecule, comprising a nucleotide sequence comprising a sequence of at least 20 consecutive nucleotide bases, wherein said synthetic polynucleotide molecule is capable of binding to a pre-mRNA transcript of the CFTR gene, and suppressing intron 22 cryptic exon inclusion in the mature CFTR mRNA. The phrase "suppress intron 22 cryptic exon inclusion" as used herein refers to lowering the occurrence of the addition of 84 nucleotides (SEQ ID NO: 5) found within intron 22 of the CFTR gene to the mature CFTR mRNA, leading to degradation of said mRNA by the nonsense mediated mRNA decay (NMD) mechanism, as illustrated in FIG. 6. In certain embodiments, said nucleotide sequence is complementary to the nucleotide sequence set forth in SEQ ID NO: 3, or to a fragment thereof. In other certain embodiments, said nucleotide sequence comprises a nucleotide sequence set forth in SEQ ID NO: 6, SEQ ID NO: 7, SEQ ID NO: 8 or SEQ ID NO: 9. Each possibility represents a separate embodiment of the present invention.

The present invention further provides, in a related aspect, a pharmaceutical composition comprising a synthetic polynucleotide molecule as described above, and a pharmaceutically acceptable carrier.

In a further related aspect, the present invention provides a synthetic polynucleotide molecule as described above, for use in the modulation of splicing of a CFTR pre-mRNA. In certain embodiments, said synthetic polynucleotide molecule is for use in reducing the level of an mRNA molecule comprising the nucleotide sequence set forth in SEQ ID NO: 11. In other certain embodiments, said synthetic polynucleotide molecule is for use in increasing the level of an mRNA molecule comprising the nucleotide sequence set forth in SEQ ID NO: 1. In other certain embodiments, said synthetic polynucleotide molecule comprises the nucleotide sequence set forth in SEQ ID NO: 6, SEQ ID NO: 7, SEQ ID NO: 8 or SEQ ID NO: 9. Each possibility represents a separate embodiment of the present invention.

The invention further provides, in an aspect, a method for improving at least one clinical parameter of Cystic Fibrosis in a patient in need thereof, comprising the step of administering a therapeutically effective amount of a synthetic polynucleotide molecule as described above to said patient. In certain embodiments, said clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the present invention.

BRIEF DESCRIPTION OF THE DRAWINGS

FIG. 2: illustrates the binding site (underlined) of oligonucleotide 5 used to suppress aberrant splicing of exon 10 of the CFTR gene. Small case sequences—intron 9 and intron 10, respectively. Upper case sequence—exon 10.

FIG. 8A-8B: illustrates the effect of oligonucleotides 1-4 on (8A) CFTR 84 bp splicing variant mRNA levels, and on (8B) total CFTR mRNA levels. Specific oligonucleotides were transfected (Lipofectamine, Invitrogen) into CFP15a epithelial cell line carrying the 3849+10 kb C to T splicing mutation (transfection concentration: 10 nM and 25 nM). Total RNA was extracted from the cells 24 hours after transfection and cDNA was amplified by RT-PCR followed by nested PCR. Following oligonucleotides treatment, a marked elevation in the level of correctly spliced transcript (total CFTR) was observed. Under the same conditions aberrantly spliced transcripts were undetectable.

DETAILED DESCRIPTION OF THE INVENTION

The present invention provides oligonucleotides and compositions comprising said oligonucleotides, capable of binding to a CFTR pre-mRNA, thereby modulating splicing and restoring or enhancing the function of the CFTR gene product. The present invention thus identifies sequences within the CFTR pre-mRNA which are targeted in order to modulate the splicing cascade of the CFTR pre-mRNA. Modulating CFTR pre-mRNA splicing, as demonstrated in the present invention, can avoid improper skipping of canonical exons and can also avoid improper recognition of intron sequences as exons. As a result of the modulation of splicing, a functional CFTR protein is produced by an otherwise aberrant CFTR allele.

The present invention stems in part from the finding that artificial "anti-sense" polynucleotide molecules are able to target and bind predetermined sequences at the pre-mRNA molecule of the CFTR gene, and that said binding modulates the splicing of said pre-mRNA molecule into mature mRNA, which subsequently translates into a functional CFTR protein. The targets within a CFTR pre-mRNA molecule are those discovered to be involved in splicing, either indirectly, by affecting the splicing of adjacent as well as remote sequences, or directly, by affecting their own splicing.

Thus, in one aspect, the present invention provides a synthetic polynucleotide molecule, comprising a nucleotide sequence comprising a sequence of at least 18 consecutive nucleotide bases, wherein said synthetic polynucleotide molecule is capable of binding to a pre-mRNA transcript of the CFTR gene, and suppressing exon 10 exclusion from the mature CFTR mRNA.

The phrase "a nucleotide sequence comprising a sequence of at least 18 consecutive nucleotide bases" as used herein refers to a sequence of at least 18 consecutive nucleotides linked by a backbone, wherein each nucleotide comprises a base. In certain embodiments, said base is selected from the group consisting of adenine, guanine, cytosine, uracil and optionally thymine. In other certain embodiments, said base is selected from the group consisting of adenine, guanine, cytosine and uracil. Each possibility represents a separate embodiment of the present invention.

Figure 1:
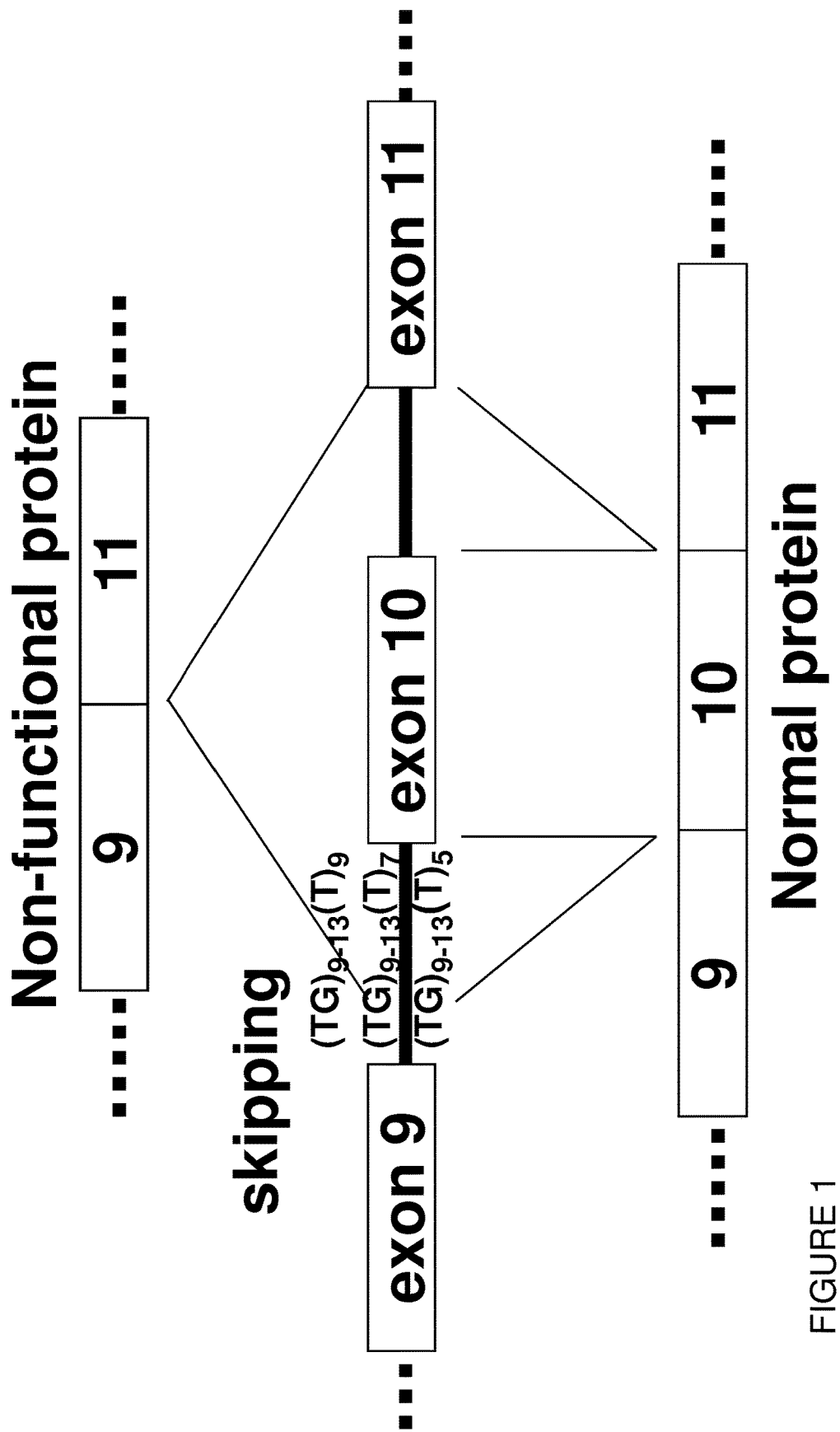
FIG. 1: illustrates the effect of aberrant splicing of exon 10 of the CFTR gene. Bottom—upon normal splicing, exons 9 becomes adjacent to exon 10, and exon 10 becomes adjacent to exon 11. Middle—the poly $(TG)_n(T)_n$ tract at the acceptor splice site of exon 10 affects the retention of this exon in the mature mRNA, $(TG)_{13}(T)_5$ generating the highest skipping levels. Top—the skipping of the exon results in a non-functional gene transcript.

The phrase "suppressing exon 10 exclusion" as used herein refers to lowering the occurrence of the exclusion of exon 10 from the mature CFTR mRNA (as in SEQ ID NO: 12), also known as "exon 10 skipping", which upon translation results in a non-functional protein, as illustrated in FIG. 1.

In certain embodiments, the nucleotide sequence comprises at least 18 nucleotides e.g. at least 18, at least 19, at least 20 or at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention.

In order to suppress exon 10 exclusion, the synthetic polynucleotide must bind to an exon 10 splicing-silencing-motif found within and/or adjacent to exon 10 of the CFTR gene. Thus, in certain embodiments, the nucleotide sequence is complementary to the nucleotide sequence set forth in SEQ ID NO: 2, or to a fragment thereof. Each possibility represents a separate embodiment of the present invention.

The term "exon 10 splicing-silencing-motif" as used herein refers to negatively acting elements involved in exon recognition, i.e any nucleotide sequences within the CFTR pre-mRNA, the binding of which by an exogenous agent, e.g. the oligonucleotides of the present invention, decreases the incidence of exon 10 skipping, increases the incidence of exon 10 inclusion, and/or increasing the level of full length normal CFTR mRNA (as assessed by conventional methods, e.g. by RT-PCR across the CFTR mRNA transcripts).

The phrase "or to a fragment thereof" as used herein refers to any consecutive fragment of the nucleotide sequence in SEQ ID NO: 2 or SEQ ID NO: 3, which is at least equal in length to the nucleotide sequence comprised in the synthetic polynucleotide. For example, if the synthetic polynucleotide molecule of the present invention comprises a sequence of 18 consecutive nucleotides, the fragment of the nucleotide sequence in SEQ ID NO: 2 or SEQ ID NO: 3 to which it binds is also 18 nucleotides in length.

In certain embodiments, said nucleotide sequence comprises a nucleotide sequence set forth in SEQ ID NO: 10 or an active fragment of said nucleotide sequence. Each possibility represents a separate embodiment of the present invention.

The phrase "active fragment of a nucleotide sequence" as used herein refers to a fragment that is 100% identical to a contiguous portion of the full nucleotide sequence, providing that at least about 30%, 40%, 50%, 60%, 70%, 80% or 90% of the activity of the original nucleotide sequence is retained. Each possibility represents a separate embodiment of the present invention.

According to some embodiments, said active fragment consists at least about 30%, 40%, 50%, 60%, 70%, 80% or 90% of the original nucleotide sequence. Each possibility represents a separate embodiment of the present invention.

The interaction between the synthetic polynucleotide molecule of the present invention and their target, a CFTR pre-mRNA, is primarily a base-base interaction, wherein the nucleotides of the synthetic polynucleotide molecule of the present invention have a base sequence complementary to the base sequence of their target CFTR pre-mRNA. It therefore should be understood that the type of backbone used to link the nucleotides of the synthetic polynucleotide molecule of the present invention is secondary, as long as it is known to a man of average skill in the art to be appropriate for carrying bases for targeting single stranded DNA and/or RNA molecules. Many such backbones are long known in the art, including the following non-limiting examples of a phosphate-ribose backbone (as in RNA), a phosphate-deoxyribose backbone (as in DNA), a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone, all of which are considered appropriate backbones according to the present invention, and each possibility represents a separate embodiment of the present invention.

In certain embodiments, said backbone is selected from the group consisting of a phosphorothioate backbone, a 2'-O-methyl-phosphorothioate (2OMP) backbone, a phosphorodiamidate morpholino (PMO) backbone, a peptide nucleic acid (PNA) backbone, a 2-methoxyethyl phosphorothioate (MOE) backbone, and an alternating locked nucleic acids (LNAs) backbone. In more specific embodiments, said backbone is selected from the group consisting of a phosphorothioate backbone, a 2'-O-methyl-phosphorothioate (2OMP) backbone, a phosphorodiamidate morpholino (PMO) backbone and a 2-methoxyethyl phosphorothioate (MOE) backbone. Each possibility represents a separate embodiment of the present invention.

In another aspect, the present invention provides a pharmaceutical composition comprising a synthetic polynucleotide molecule as described above, and a pharmaceutically acceptable carrier.

The term "pharmaceutically acceptable carrier" as used herein refers to any of the standard pharmaceutical carriers known in the field such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising such carriers are formulated by well-known conventional methods. Depending on the intended mode of administration and the intended use, the compositions may be in the form of solid, semi-solid, or liquid dosage forms, such, for example, as powders, granules, crystals, liquids, suspensions, liposomes, nanoparticles, nano-emulsions, pastes, creams, salves, etc., and may be in unit-dosage forms suitable for administration of relatively precise dosages.

In certain embodiments, the pharmaceutical composition is formulated for oral, nasal, aerosol, inhalational, abdominal, subcutaneous, intra-peritoneal or intravenous administration. Each possibility represents a separate embodiment of the present invention.

Figure 5:
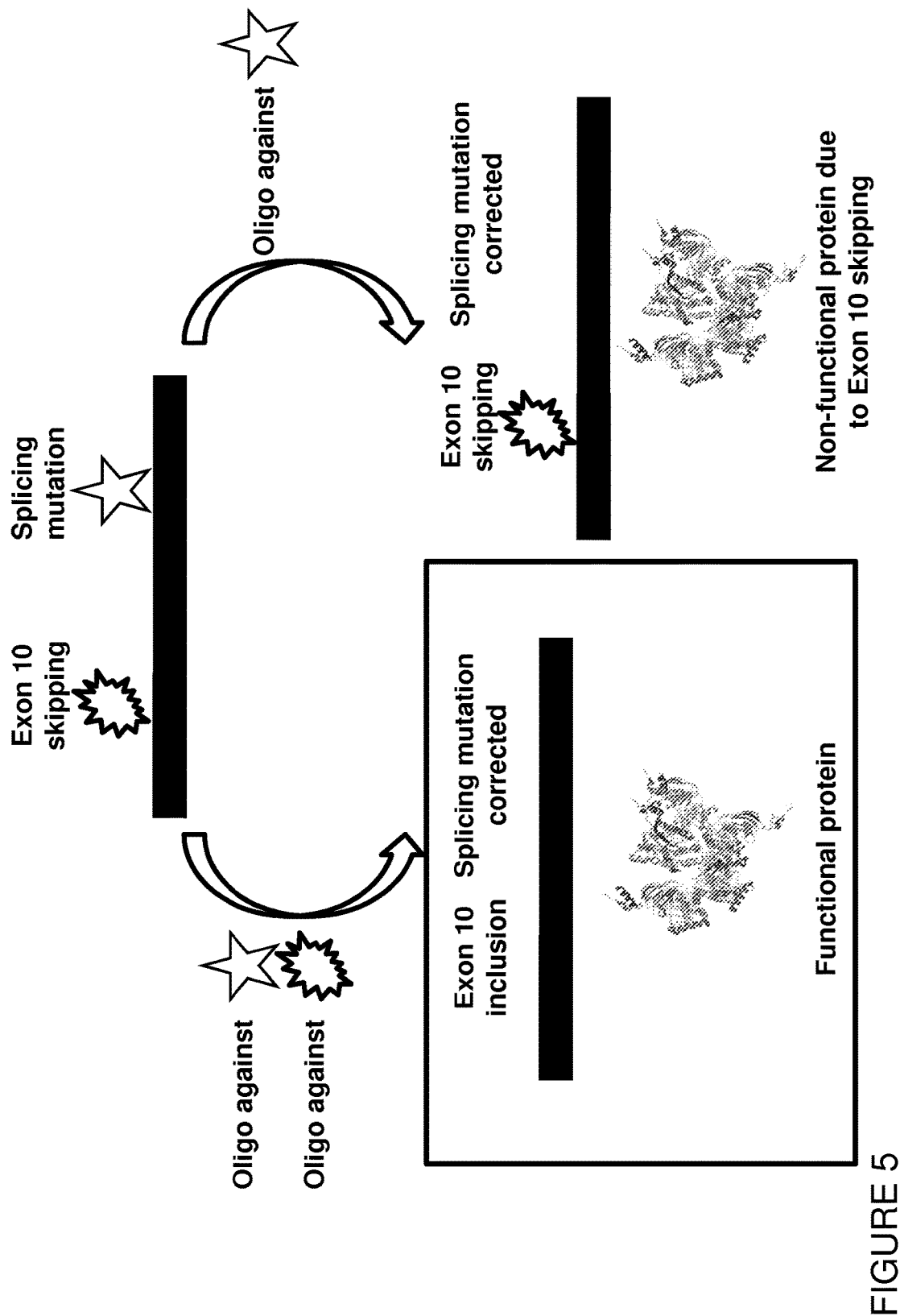
FIG. 5: illustrates the advantage of combining oligonucleotides targeted to correct CFTR exon 10 skipping with other CFTR therapies, e.g. oligonucleotides targeted to correct CFTR splicing mutation.

Being a long-known and well-studied disease, certain drugs and agents are known in the art for the treatment of Cystic Fibrosis patients. Administrating a synthetic polynucleotide molecule according to the present invention with one or more of these drugs may be crucial in achieving beneficial therapeutic results (see e.g. FIG. 5). Thus, in certain embodiments, the pharmaceutical composition of the present invention further comprises at least one additional anti-Cystic-Fibrosis agent.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl] benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

According to other embodiments, the pharmaceutical composition comprises the synthetic polynucleotide molecule described above, capable of suppressing exon 10 exclusion from the mature CFTR mRNA, and a synthetic polynucleotide molecule, capable of suppressing intron 22 cryptic exon inclusion in the mature CFTR mRNA.

In an embodiment, the pharmaceutical composition comprises the synthetic polynucleotide molecule described above, capable of suppressing exon 10 exclusion from the mature CFTR mRNA, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule, capable of suppressing intron 22 cryptic exon inclusion in the mature CFTR mRNA. Each possibility represents a separate embodiment of the present invention.

In an embodiment, the pharmaceutical composition comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8 or SEQ ID NO: 9. Each possibility represents a separate embodiment of the present invention.

In another aspect, the present invention provides a synthetic polynucleotide molecule as described above, for use in the modulation of splicing of a CFTR pre-mRNA. The phrase "modulation of splicing" as used herein refers to affecting a change in the level of any RNA or mRNA variant produced by the CFTR native pre-mRNA, e.g. causing an increase or decrease in the level of abnormal CFTR mRNA not comprising exon 10, causing an increase or decrease in the level of normal, full CFTR mRNA, and/or causing an increase or decrease in the level of abnormal CFTR RNA or mRNA comprising a premature termination codon (nonsense codon). It is therefore evident that any change in ratio between certain CFTR splicing variants is also considered to be the result of splicing modulation. Each possibility represents a separate embodiment of the present invention.

Thus, according to certain embodiments, the synthetic polynucleotide molecule described above is for use in the modulation of splicing of a CFTR pre-mRNA carrying a mutation of CFTR mutation classes I to V, especially of classes IV and V. Each possibility represents a separate embodiment of the present invention. In certain such embodiments, the synthetic polynucleotide molecule described above is for use in correcting or improving chloride transport through the CFTR channel, or in increasing the production of functional CFTR protein. Each possibility represents a separate embodiment of the present invention. In other certain such embodiments, the synthetic polynucleotide molecule described above is for use in patients carrying CFTR mutations with residual CFTR function such as mutations of mutation classes I to V, preferably classes IV and/or V. Each possibility represents a separate embodiment of the present invention.

According to other certain embodiments, the synthetic polynucleotide molecule described above is for use in reducing the level of an mRNA molecule comprising the nucleotide sequence set forth in SEQ ID NO: 12.

In other embodiments, the synthetic polynucleotide molecule described above is for use in increasing the level of an mRNA molecule comprising the nucleotide sequence set forth in SEQ ID NO: 1.

In certain embodiments, the synthetic polynucleotide described above comprises the nucleotide sequence set forth in SEQ ID NO: 10, or an active fragment of said nucleotide sequence. Each possibility represents a separate embodiment of the present invention.

In a further aspect, the present invention provides a method for improving at least one clinical parameter of Cystic Fibrosis in a patient in need thereof, comprising the step of administering a therapeutically effective amount of a synthetic polynucleotide molecule as described above to said patient. Being a genetic disease, Cystic Fibrosis currently cannot be cured, but its clinical manifestations and/or symptoms can be treated by the oligonucleotides of the present invention, for a marked increase and/or improvement in a patient's clinical status and quality of life.

The term "improving" as used herein refers to a favorable change, i.e. an increase or a decrease of at least 5%, at least 10%, at least 15%, at least 20%, at least 25%, at least 30%, at least 35%, at least 40%, at least 45%, or at least 50% in a certain Cystic Fibrosis clinical parameter.

The term "a therapeutically effective amount" as used herein refers to an amount necessary for improving at least one clinical parameter of Cystic Fibrosis or reducing the severity of at least one clinical parameter of Cystic Fibrosis in a patient. The therapeutically effective amount differs according to the patient's status, the synthetic polynucleotide molecule's administration route, excipient usage and co-usage of other active agents.

Thus, in certain embodiments, the clinical parameter is selected from the group consisting of lung function, time to the first pulmonary exacerbation, a change in weight, a change in height, a change in Body Mass Index (BMI), a change in the concentration of sweat chloride, number and/or duration of pulmonary exacerbations, total number of days of hospitalization for pulmonary exacerbations, or the need for antibiotic therapy for sinopulmonary signs or symptoms. Each possibility represents a separate embodiment of the present invention.

In certain embodiments, the method further comprises administering at least one additional anti-Cystic-Fibrosis agent to said patient.

In certain such embodiments, said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

In certain embodiments, the method comprises administering the synthetic polynucleotide molecule as described above, capable of suppressing exon 10 exclusion from the mature CFTR mRNA, and further administering a synthetic polynucleotide molecule, capable of suppressing intron 22 cryptic exon inclusion in the mature CFTR mRNA.

In certain such embodiments, the method comprises administering the synthetic polynucleotide molecule as described above, capable of suppressing exon 10 exclusion from the mature CFTR mRNA, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule, capable of suppressing intron 22 cryptic exon inclusion in the mature CFTR mRNA. Each possibility represents a separate embodiment of the present invention.

In certain such embodiments, the method comprises administering a synthetic polynucleotide molecule comprising the nucleotide sequence set forth in SEQ ID NO: 10 or an active fragment of said nucleotide sequence, and further administering a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, the administration of said therapeutically effective amount of a synthetic polynucleotide molecule of the present invention and the administration of said at least one additional anti-Cystic-Fibrosis agent are independently oral, nasal, aerosol, inhalational, abdominal, subcutaneous, intra-peritoneal or intravenous administration. Each possibility represents a separate embodiment of the present invention. It should be understood that the selection of an administration route depends on the nature of the therapeutic agent and the site of its intended effect, and thus certain agents may be administrated via the same or different administration routes.

In a further aspect, the present invention provides a kit comprising a synthetic polynucleotide molecule as described above, and an additional anti-Cystic-Fibrosis agent. In certain embodiments said additional anti-Cystic-Fibrosis agent is selected from the group consisting of a CFTR-splicing-modulating agent, a CFTR potentiator and a CFTR corrector. Each possibility represents a separate embodiment of the present invention.

In a more specific such embodiment, said CFTR-splicing-modulating agent is a synthetic polynucleotide molecule capable of suppressing intron 22 cryptic exon inclusion in the mature CFTR mRNA. In another more specific such embodiment, said CFTR potentiator is N-(2,4-Di-tert-butyl-5-hydroxyphenyl)-4-oxo-1,4-dihydroquinoline-3-carboxamide (Ivacaftor). In another more specific such embodiment, said CFTR corrector is selected from the group consisting of 3-[5-(2-fluorophenyl)-1,2,4-oxadiazol-3-yl]benzoic acid (Ataluren) and 3-{6-{[1-(2,2-difluoro-1,3-benzodioxol-5-yl)cyclopropanecarbonyl]amino}-3-methylpyridin-2-yl}benzoic acid (Lumacaftor). Each possibility represents a separate embodiment of the present invention.

In other certain embodiments, said kit comprises a synthetic polynucleotide molecule as described above, capable of suppressing exon 10 exclusion from the mature CFTR mRNA, and a synthetic polynucleotide molecule, capable of suppressing intron 22 cryptic exon inclusion in the mature CFTR mRNA.

In specific such embodiments, said kit comprises a synthetic polynucleotide molecule as described above, capable of suppressing exon 10 exclusion from the mature CFTR mRNA, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule, capable of suppressing intron 22 cryptic exon inclusion in the mature CFTR mRNA. Each possibility represents a separate embodiment of the present invention.

In specific such embodiments, said kit comprises a synthetic polynucleotide molecule comprising the nucleotide sequence set forth in SEQ ID NO: 10 or an active fragment of said nucleotide sequence, and a synthetic polynucleotide molecule comprising the nucleotide sequence set forth in SEQ ID NO: 6, SEQ ID NO: 7, SEQ ID NO: 8, or SEQ ID NO: 9. Each possibility represents a separate embodiment of the present invention.

In certain embodiments, said synthetic polynucleotide and said additional anti-Cystic-Fibrosis agent are comprised in one or more pharmaceutical compositions. In certain embodiments, said synthetic polynucleotide and said additional anti-Cystic-Fibrosis agent are comprised in the same or different pharmaceutical compositions. In other certain embodiments, said one or more pharmaceutical compositions are each independently formulated for oral, nasal, aerosol, inhalation, abdominal, subcutaneous, intra-peritoneal or intravenous administration. Each possibility represents a separate embodiment of the present invention.

Figure 6:
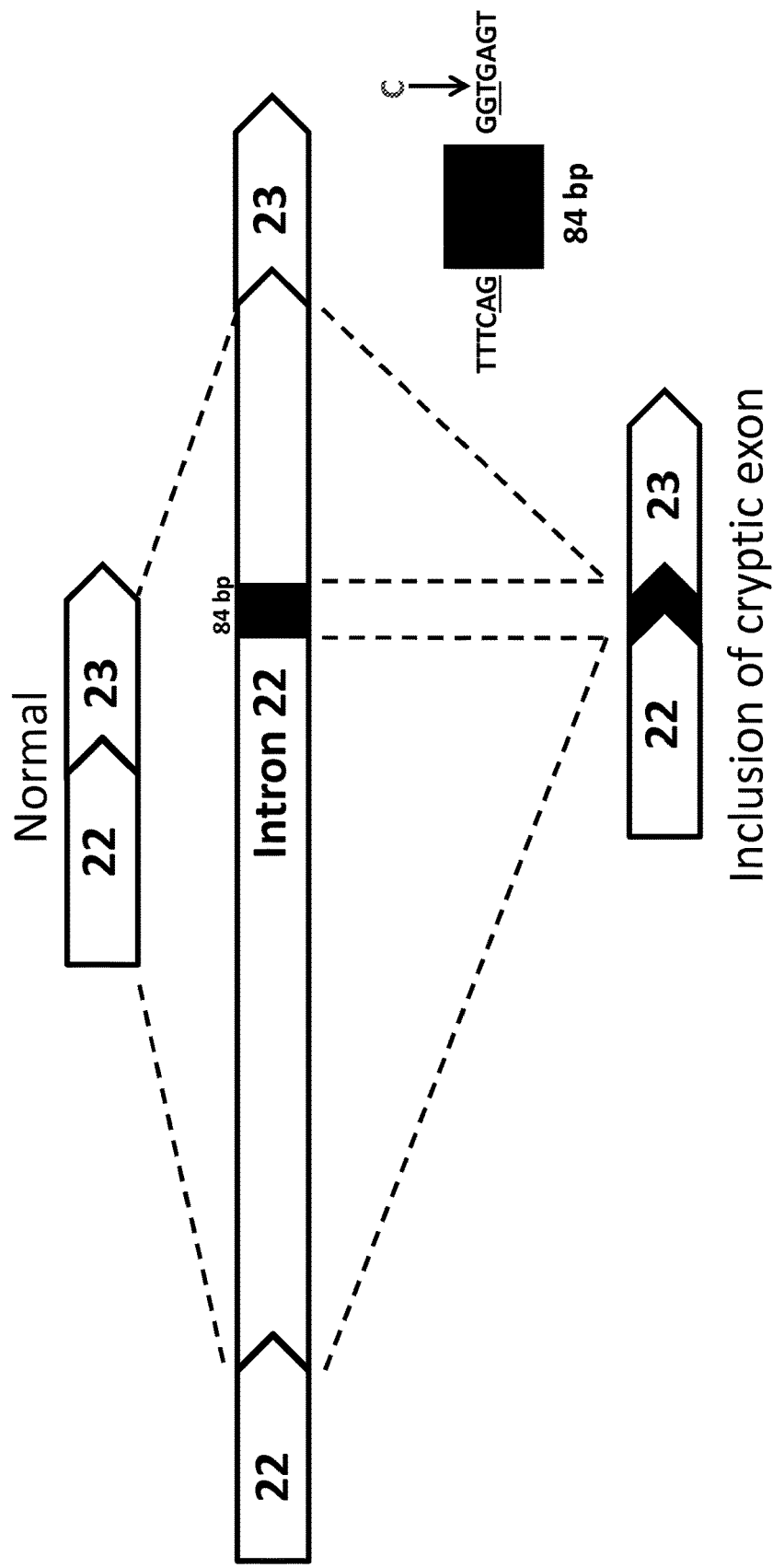
FIG. 6: illustrates the effect of the 3849+10 kb C to T mutation in intron 22 of the CFTR gene. Top—upon normal splicing, exon 22 and exon 23 become adjacent. Bottom—a splicing mutation in intron 22 (denoted "3849+10 kb C-to-T" mutation) leads to inclusion of an excess of 84 bases in the mature CFTR mRNA (denoted "intron 22 cryptic exon"). The mutation creates a premature in-frame stop codon, leading to mRNA degradation by the nonsense mediated mRNA decay (NMD) mechanism.

In a further aspect, the present invention provides a synthetic polynucleotide molecule, comprising a nucleotide sequence comprising a sequence of at least 20 consecutive nucleotide bases, wherein said synthetic polynucleotide molecule is capable of binding to a pre-mRNA transcript of the CFTR gene, and suppressing intron 22 cryptic exon inclusion in the mature CFTR mRNA. The phrase "suppress intron 22 cryptic exon inclusion" as used herein refers to lowering the occurrence of the addition of 84 nucleotides (SEQ ID NO: 5) found within intron 22 of the CFTR gene to the mature CFTR mRNA, leading to degradation of said mRNA by the nonsense mediated mRNA decay (NMD) mechanism, as illustrated in FIG. 6. In certain embodiments, the nucleotide sequence comprises at least 20 nucleotides e.g. at least 21 nucleotides. In other certain embodiments, the nucleotide sequence comprises about 20 to 30 nucleotides e.g. about 20 to 28, about 20 to 26 or about 22 to 26 nucleotides. In specific embodiments, the nucleotide sequence comprises 22, 23, 24, 25, or 26 nucleotides. Each possibility represents a separate embodiment of the present invention. In certain embodiments, said nucleotide sequence is complementary to the nucleotide sequence set forth in SEQ ID NO: 3, or to a fragment thereof. In certain embodiments, said nucleotide sequence is complementary to the nucleotide sequence set forth in SEQ ID NO: 4, or to a fragment thereof. Each possibility represents a separate embodiment of the present invention. In other certain embodiments, said nucleotide sequence comprises a nucleotide sequence set forth in SEQ ID NO: 6, SEQ ID NO: 7, SEQ ID NO: 8 or SEQ ID NO: 9. Each possibility represents a separate embodiment of the present invention. Specific embodiments of said synthetic polynucleotide molecule are described above.

The present invention further provides, in a related aspect, a pharmaceutical composition comprising a synthetic polynucleotide molecule as described above, and a pharmaceutically acceptable carrier. Specific embodiments of said pharmaceutical composition are described above.

In a further related aspect, the present invention provides a synthetic polynucleotide molecule as described above, for use in the modulation of splicing of a CFTR pre-mRNA. In certain embodiments, said synthetic polynucleotide molecule is for use in reducing the level of an mRNA molecule comprising the nucleotide sequence set forth in SEQ ID NO: 11. In other certain embodiments, said synthetic polynucleotide molecule is for use in increasing the level of an mRNA molecule comprising the nucleotide sequence set forth in SEQ ID NO: 1. In other certain embodiments, said synthetic polynucleotide molecule comprises the nucleotide sequence set forth in SEQ ID NO: 6, SEQ ID NO: 7, SEQ ID NO: 8 or SEQ ID NO: 9. Each possibility represents a separate embodiment of the present invention. Specific embodiments of said use are described above.

The invention further provides, in an aspect, a method for improving at least one clinical parameter of Cystic Fibrosis in a patient in need thereof, comprising the step of administering a therapeutically effective amount of a synthetic polynucleotide molecule as described above to said patient. In certain embodiments, said clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms. Each possibility represents a separate embodiment of the present invention. Specific embodiments of said method are described above.

The terms "comprises", "comprising", "includes", "including", "having" and their conjugates mean "including but not limited to". This term encompasses the terms "consisting of" and "consisting essentially of". As used herein, the singular form "a", "an", "the" and "said" include plural references unless the context clearly dictates otherwise. For example, the term "a compound" or "at least one compound" may include a plurality of compounds, including mixtures thereof.

The following examples are meant to be construed as non-limiting to the scope of the invention and are to serve merely as illustrative embodiments.

EXAMPLES

TABLE 1

Sequences.

| SEQ ID NO | Title | Chr. 7 position | Orientation |
|---|---|---|---|
| 1 | Mature CFTR mRNA | NM_000492.3 (NCBI) | Sense |
| 2 | Exon 10 target | 117188295-117189277 | Sense |
| 3 | Intron 22 target #1 | 117279911-117280032 | Sense |
| 4 | Intron 22 target #2 | 117279906-117280037 | Sense |
| 5 | Intron 22 cryptic exon | 117279930-117280013 | Sense |
| 6 | Oligonucleotide #1 | 117279925-117279949 | Anti-sense |
| 7 | Oligonucleotide #2 | 117279939-117279963 | Anti-sense |
| 8 | Oligonucleotide #3 | 117279975-117279999 | Anti-sense |
| 9 | Oligonucleotide #4 | 117280007-117280031 | Anti-sense |
| 10 | Oligonucleotide #5 | 117188920-117188941 | Anti-sense |
| 11 | Exons 1-27 + cryptic exon 22 | | Sense |
| 12 | Exons 1-9 + 11-27 | | Sense |

TABLE 1-continued

Sequences.

| SEQ ID NO | Title | Chr. 7 position | Orientation |
|---|---|---|---|
| 13 | Control Oligonucleotide #1 | | Anti-sense |
| 14 | Control Oligonucleotide #2 | | Anti-sense |

TABLE 2

Oligonucleotides.

| Oligonucleotide # | SEQ ID NO: | Nucleotide sequence | Length (nt) |
|---|---|---|---|
| 1 | 6 | aaaucaagaugacaagucaacugaa | 25 |
| 2 | 7 | cuugugguccagaaaucaagaug | 25 |
| 3 | 8 | aacagauggaagacucuuguaauua | 25 |
| 4 | 9 | ucagggugucuuacucaccauuuua | 25 |
| 5 | 10 | cuagaaaaaaaagagacaugg | 22 |
| 6 | 13 | cuugugaaacuuacugauuaucagg | 25 |
| 7 | 14 | ccucuuaccucaguuacaauuuaua | 25 |

Methods

Oligonucleotide Synthesis

2-O-Methyl modified oligonucleotides on a phosphorothioate backbone were synthesised on an Expedite 8909 Nucleic Acid Synthesiser (Life Technologies) using the 1 umol thioate synthesis protocol according to the pre-programmed synthesis manual. The synthesis protocols are pre-loaded on the Synthesizer.

Cell Culture and Transfection Protocol for Intron 22 Cryptic Exon Exclusion

CFP15a nasal epithelial cell line, established from a patient heterozygous for W1282X and 3849+10 kb C to T mutations, were grown in Bronchial Epithelial Cell Basal medium (Lonza). One day prior to transfection, the cells were plated onto 140 mm plates with 400,000 cells per plate. On the day of transfection, the medium was replaced to opti-MEM (Invitrogen) with no additional supplements. Cells were transfected with 2-O-methyl AO lipoplexes (Lipofectamin:AO ratio of 1:1) with AO concentrations of 25 nM or 10 nM and left to incubate at 37° C. for 24 hours. After 4 hours of incubation, the transfection medium was replaced with fresh Bronchial Epithelial Cell Basal medium.

RNA Analysis

TABLE 3

Primer Sequences.

| Primer | Primer location | Sequence 5'->3' |
|---|---|---|
| 1[a] | External CFTR Fwd | AGCATTTGCTGATTGCACAG (SEQ ID NO: 15) |
| 2[a] | External CFTR Rev | GAAAGAGCTTCACCCTGTCG (SEQ ID NO: 16) |
| 3[b] | Short CFTR (ex 26) Fwd | AATGCTGGAATGCCAACAATT (SEQ ID NO: 17) |
| 4[b] | Short CFTR (ex 27) Rev | GGCTCCTCTCGTTCAGCAGT (SEQ ID NO: 18) |
| 5[a] | 84 external Fwd (exon 22) | GGGCCAAATGACTGTCAAAG (SEQ ID NO: 19) |
| 6[a] | 84 external Rev (84 bp) | GCAACAGATGGAAGACTCTTGT (SEQ ID NO: 20) |
| 7[b] | TPW Fwd (exon 22) | GCCATATTAGAGAACATTTCCTTCTCA (SEQ ID NO: 21) |
| 8[b] | TPW Rev (84 bp) | ACCTTGTGGTCTCCAGAAATCAA (SEQ ID NO: 22) |

[a]-RT-PCR; [b]-nested PCR.

Total RNA was extracted using the RNeasy extraction kit (QIAGEN). RNA-less and reverse-transcriptase-less reactions were used as controls. 1000 ng of total RNA was used for complementary DNA (cDNA) synthesis using the High Capacity cDNA Reverse Transcription Kit (Applied Biosystems). 1 μl of cDNA was used for RT-PCR (Invitrogen Amplitaq enzyme kit) using outer primers targeting sequences at the extremities of exons 26/27 (primers 1 and 2) and of exon 22/84 bp pseudo exon (primers 5 and 6). Samples were incubated at 94° C. for 1:45 min, followed by 35 cycles (for 84 bp variant amplification) or 30 cycles (for total CFTR amplification) of 94° C. for 30 sec, 55° C. for 30 sec and 72° C. for 1 min. Samples were diluted 1/27 and 1/81 and 3 μl were used for nested PCR for second amplification using primers targeting internal regions across exon 22/84 bp pseudo exon (for 84 bp variant amplification, primers 7 and 8) or exons 26/27 (for total CFTR amplification, primers 3 and 4). RT-PCR was performed in ABI 7500 using a Power SYBR green PCR master Mix (Applied Biosystems). The expression level was normalized to the transcript levels of POLR2A and IPO8. Specific primers for these PCR reactions were designed using the Primer Express software. For statistical analysis Student t-test was used.

Transfection Protocol for Exon 10 Inclusion

16HBE normal bronchiole epithelial cell line shows low levels of exon 10 skipping. Cells were propagated in 10% FCS DMEM, supplemented with L-Glutamine and penicillin/streptomycin/fungizome. 16HBE cells plated onto 24 well plates with 50,000 cells per well with 10% FCS DMEM with 2 wells per treatment, and left overnight prior to transfection.

16HBE cells were transfected with 2-O-methyl oligonucleotide lipoplexes (Lipofectin:AO ratio of 2:1) with oligonucleotide concentrations of 600 nM, 300 nM and 150 nM, topped up to 1 ml with 1% FCS DMEM (no additional supplements) and left to incubate at 37° C. for 48 hours.

Nested PCR and RT-PCR Protocols

TABLE 4

Primer Sequences.

| Primer | Primer location | Sequence 5'->3' |
|---|---|---|
| 9[b] | CFTR exon 8 Fwd | GGT TCT TTG TGG TGT TTT TAT CT (SEQ ID NO: 23) |
| 10[a] | CFTR exon 8/9 Fwd | GCA ATA AAC AAA ATA CAG GAT TTC (SEQ ID NO: 24) |
| 11[a] | CFTR exon 11/12 Rev | AAA CTT GGA GAT GTC CTC TTC (SEQ ID NO: 25) |
| 12[b] | CFTR exon 12 Rev | TGC TAA AGA AAT TCT TGC TCG TT (SEQ ID NO: 26) |

[a]-nested PCR; [b]-RT-PCR.

Following transfection, cells were harvested and RNA extracted using TriZol reagent as per manufacturer's instruction. 200 ng of total RNA was used for nested PCR. Primary PCR setup using Invitrogen One Step RT-PCR SuperScript III with Platinum Taq enzyme kit as per manufacturer's instruction, amplified with primers targeting exons 8-12 (primers 9 and 12). Samples were incubated at 55° C. for 30 min, 94° C. for 2 min, followed by 35 cycles of 94° C. for 40 sec, 58° C. for 1 min and 68° C. for 1 min. Samples were diluted 1/10 and 1 ul used for secondary amplification using Invitrogen AmpliTaQ Gold enzyme kit, as per manufacturer instructions. Samples were amplified across exon 8/9 to 11/12 boundaries (primers 10 and 11) and incubated at 94° C. for 6 min, followed by 30 cycles of 94° C. for 40 sec, 55° C. for 1 min and 72° C. for 1 min. Samples were fractionated on 2% Agarose gels, and products visualized on a Chemismart-3000 gel documentation system. Product identity was confirmed by band purification and DNA sequencing as necessary.

Halide Efflux Assay (SPQ) Protocol

Cells were seeded onto collagen-coated glass coverslips and grown to ~80% confluence. Immediately prior to study, cells were hypotonically loaded with halide quenched dye 6-methoxy-N-(3-sulfopropyl)quinolinium (SPQ), 10 mM, Molecular Probes Inc., Eugene, Oreg.) for 10 min and then placed in a quenching NaI-based buffer (King & Sorscher, Biochemistry, 2000). CFTR robustly conducts iodide in addition to chloride, $HCO_3^-$, and other anions, allowing use of iodide quench as a measure of macroscopic channel activity. Cells were mounted in a specially designed perfusion chamber and fluorescence monitored using an inverted microscope. Baseline fluorescence was initially studied in NaI buffer (above) followed by dequenching $NaNO_3$ solution (King & Sorscher, Biochemistry, 2000). CFTR agonists (20 μM forskolin, 50 μM genistein) were added to activate channel gating, after which NaI buffer was again perfused. Fluorescence was normalized for each cell versus baseline and increases shown as percent above basal (quenched) values. For each coverslip, >15 individual cells were monitored. Averages from each coverslip were used for statistical analysis.

Example 1

Figure 3:
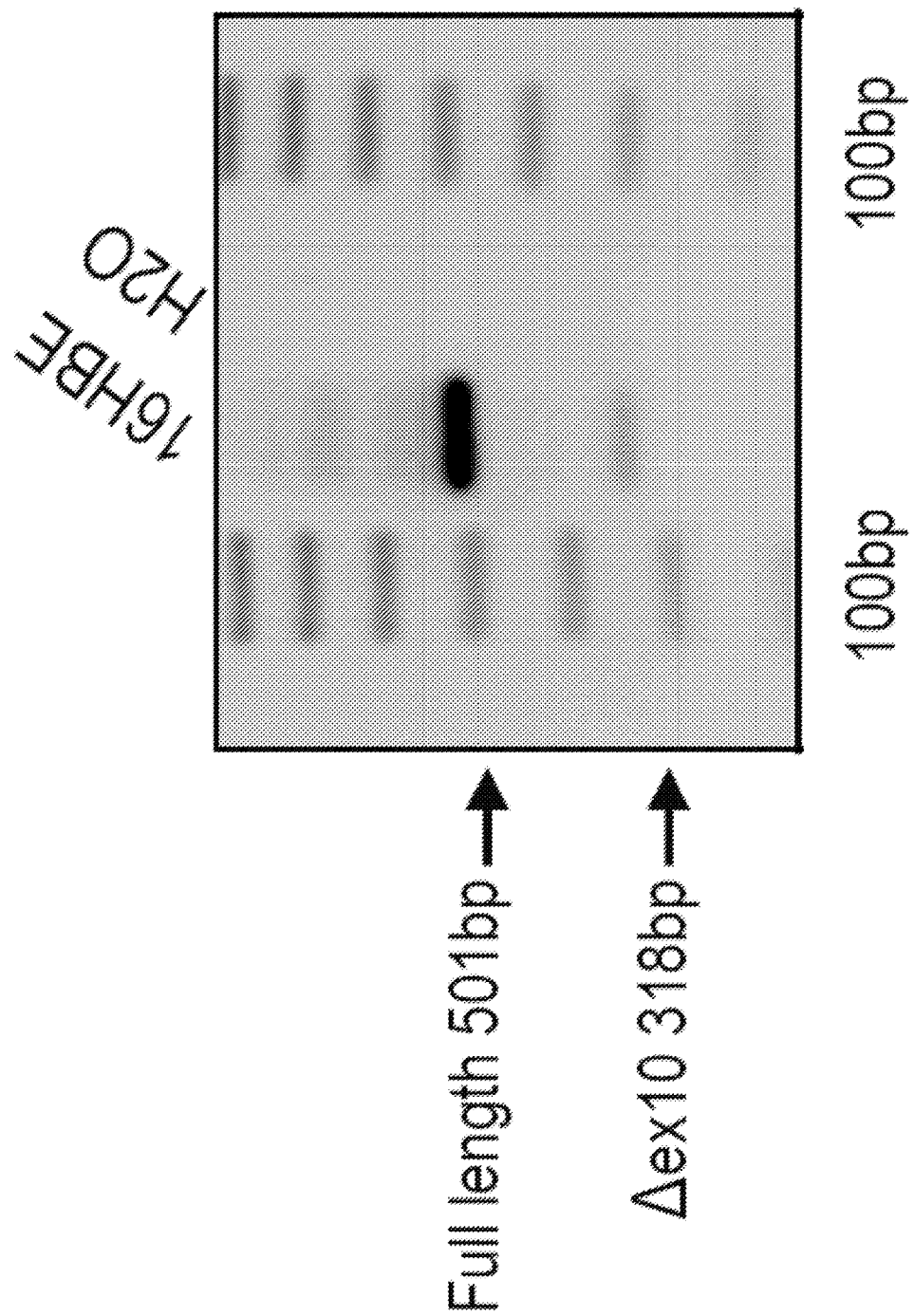
FIG. 3: illustrates the levels of base-line exon 10 skipping in untreated 16HBE cells.
Figure 4:
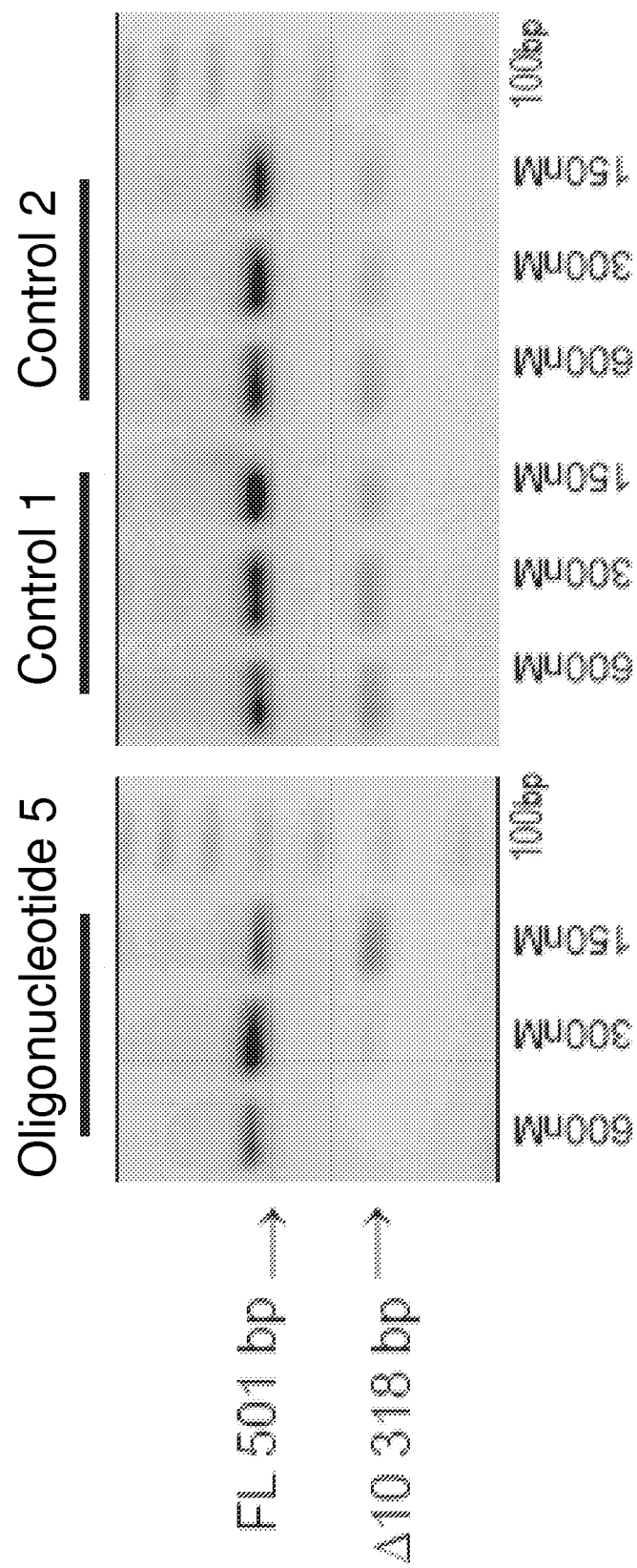
FIG. 4: illustrates the effect of oligonucleotide 5 on the correct splicing of exon 10 of the CFTR gene. FL 501 bp—variant comprising exon 10. Δ 10 318 bp—variant without exon 10.

Oligonucleotide No. 5 was synthesized and tested for its anti-splicing-silencing capability, i.e. its ability to minimize exon 10 skipping and increase exon 10 inclusion in the mature CFTR mRNA in 16HBE cells (see FIG. 3). FIG. 4 depicts that oligonucleotide no. 5 was indeed able to dramatically increase the level of exon 10 inclusion in the mature CFTR mRNA in a dose dependent manner, as clearly evident from the progressive strengthening of the full 501-base transcripts and the progressive weakening and eventually loss of the aberrant Δ exon 10 318-base transcripts.

The data presented in FIG. 4 provides substantial evidence, for the first time, that exon 10 splicing may be modulated by oligonucleotides targeting sequences within and adjacent to exon 10 (as illustrated in FIG. 2).

Example 2

Figure 7:
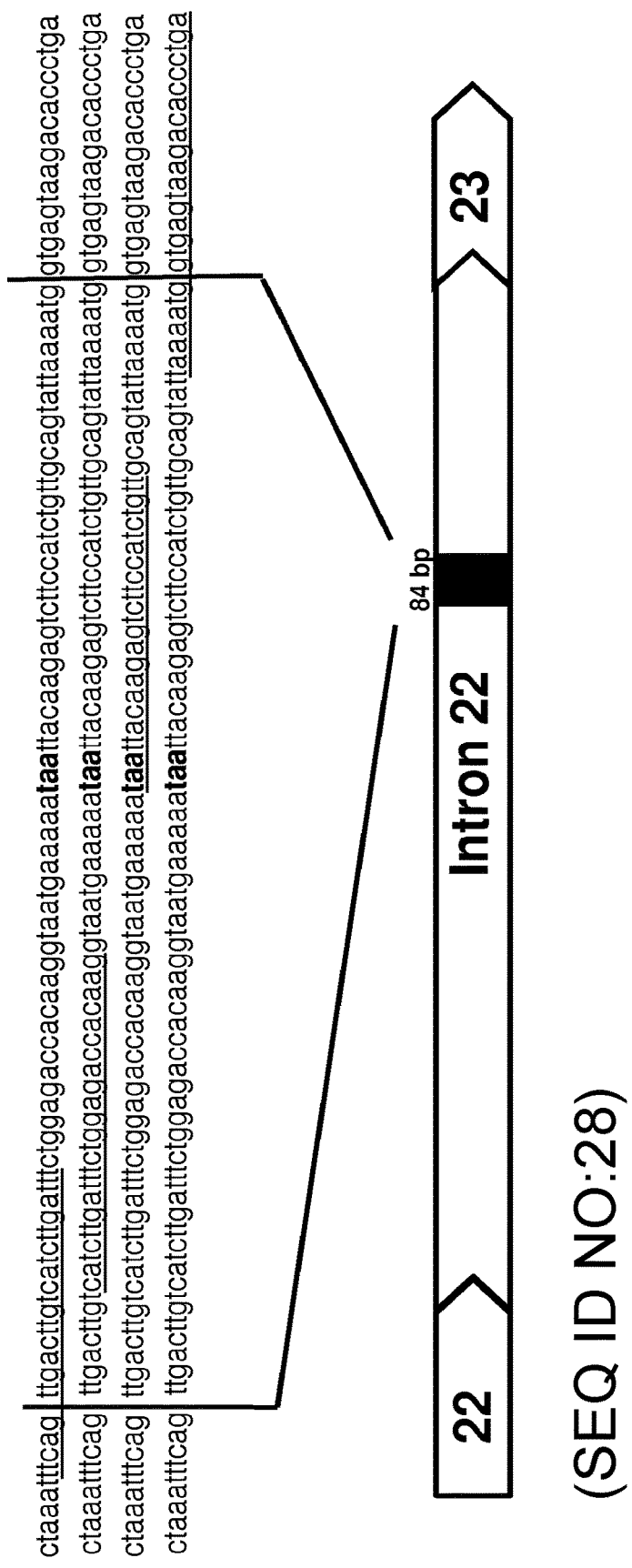
FIG. 7: illustrates the binding sites (underlined) of oligonucleotides 1-4 within the 84 bases cryptic exon (oligonucleotides 2 and 3), or at the junctions between intron 22 and the internal cryptic exon (oligonucleotides 1 and 4) in a CFTR allele carrying the 3849+10 kb C to T mutation. Bold—a premature in-frame stop codon.

Epithelial cell line CFP15a, established from a nasal polyp of a Cystic Fibrosis patient carrying the 3849+10 kb C to T splicing mutation, were transfected with various concentrations of oligonucleotides 1-4 as described above (see FIG. 7). After 4 hours of incubation, the transfected medium was replaced with fresh medium. Twenty four hours after transfection, the cells were harvested for RNA extraction, followed by cDNA synthesis. Aliquots of cDNA were used for RT-PCR using two pairs of outer primers towards exon 22 and the 84 bp cryptic exon (primers 5-6 in Table 3) and towards exon 26-27 (for total CFTR evaluation, primers 1-2 in Table 3). Nested PCR was subsequently performed using internal primers (primers 7-8 for the detection of the 84 bp cryptic exon, and primers 3-4 for the evaluation of total CFTR level). FIG. 8A depicts that oligonucleotides 1-4 completely prevented the formation of the CFTR 84 bp splicing variant in the transfected cells in both concentrations (25 and 10 nM). FIG. 8B depicts that oligonucleotides 1-4 were further able to dramatically increase by several folds the level of total CFTR mRNA.

From the data presented in FIG. 8A-B it becomes evident that oligonucleotides according to the present invention are capable of binding to their predetermined targets and significantly modify the CFTR splicing balance in cells carrying the 3849+10 kb C to T splicing mutation in favor of the full CFTR transcript.

Example 3

Figure 9:
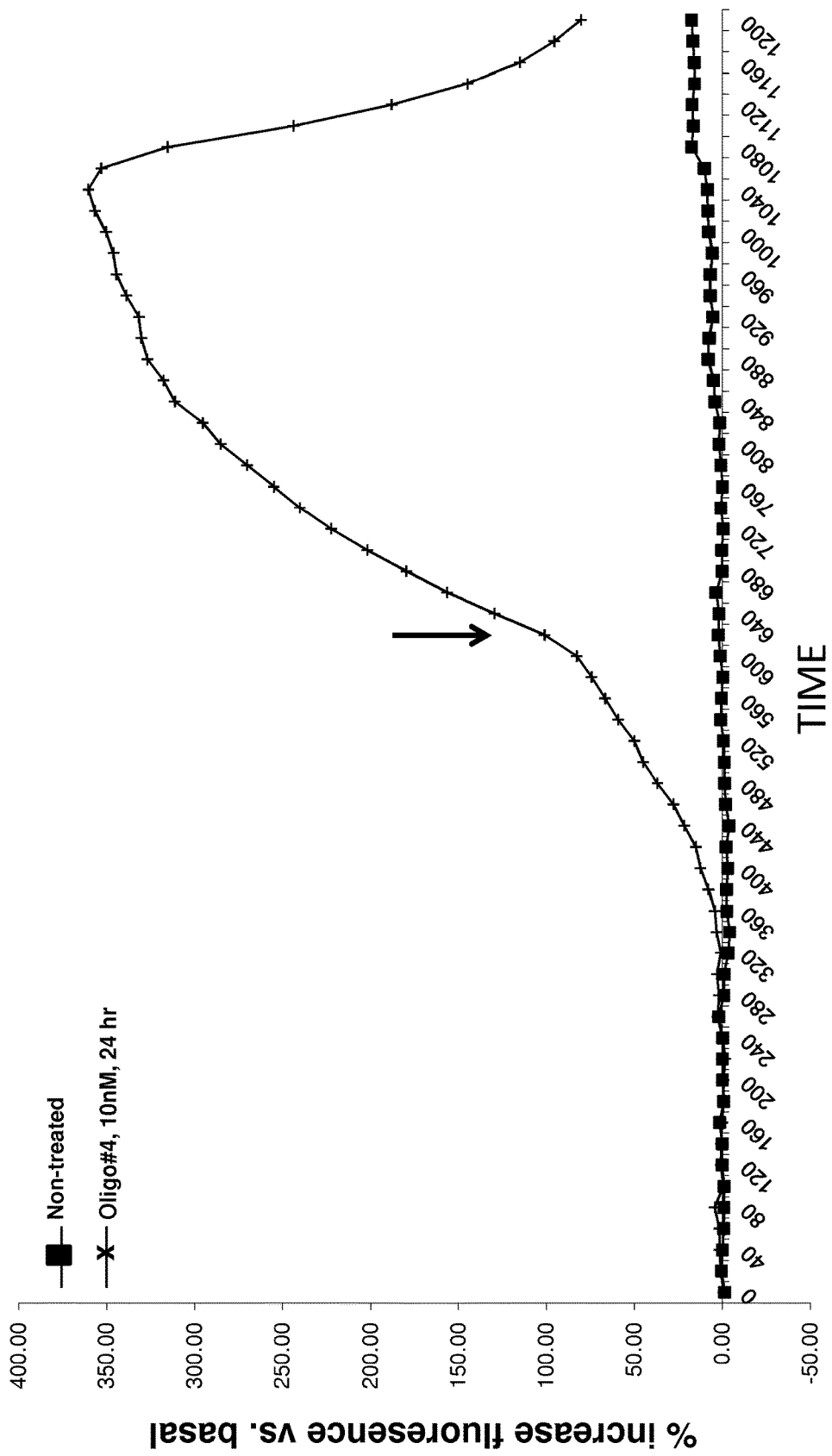
FIG. 9: illustrates the effect of oligonucleotide 4 on the restoration of the CFTR protein function. CFP15a epithelial cell line, carrying the 3849+10 kb C to T splicing mutation, were transfected with oligonucleotide 4 for 24 hours (transfection concentration: 10 nM). Following transfection, the cells were analyzed for functional CFTR activity using the halide efflux assay (SPQ). Following the oligonucleotide treatment, a significant restoration of the CFTR activity was observed. Arrow—the addition of Forskolin and Genestein, two CFTR channel activators. The extent of fluorescence is correlated with CFTR channel activation. Fluorescence was normalized versus baseline. The CFTR functional analysis of a representative cell is shown.

In addition to the experimental results provided in Example 2, CFP15a epithelial cells were transfected with oligonucleotide 4 for 24 hours (transfection concentration: 10 nM). Following transfection, the cells were analyzed for functional CFTR activity using the halide efflux assay (SPQ). Following treatment, a significant restoration of the CFTR protein activity was observed. The extent of fluorescence is correlated with CFTR channel activation. FIG. 9 depicts that as soon as 24 hours post oligonucleotide 4 transfection, functional CFTR chloride channels responsible for chloride transport were embedded in the epithelial cells' membrane resulting in restored CFTR function.

To further verify this result, forskolin and genestein (CFTR channel activators) were added, since their addition, pending that the CFTR channel is present on the cell membrane and is functional, will cause the channel to open and allow chloride efflux. FIG. 9 depicts that the fluorescent signal has increased following the addition of the activators, attributed to chloride efflux through the CFTR channel.

It is therefore evident that the administration of oligonucleotides according to the present invention is capable of substantially increasing the CFTR function in cells carrying the 3849+10 kb C to T splicing mutation.

REFERENCES

Cirak, S., Arechavala-Gomeza, V., Guglieri, M., Feng, L., Torelli, S., Anthony, K., Abbs, S., et al. (2011). Exon skipping and dystrophin restoration in patients with Duchenne muscular dystrophy after systemic phosphorodiamidate morpholino oligomer treatment: an open-label, phase 2, dose-escalation study. Lancet, 378(9791), 595-605. doi:10.1016/S0140-6736(11)60756-3

Chu C. H., Trapnell B. C., Curristin S., Cutting G. R. and Crystal R. G. (2003). Genetic basis of variable exon 9 skipping in cystic fibrosis transmembrane conductance regulator mRNA. Nature genetics, Vol. 3, 151-156

Cutting, G. R. (1990). A cluster of cystic fibrosis mutations in the first nucleotide-binding fold of the cystic fibrosis conductance regulator protein. Nature, 346(6282), 366-369

Friedman, K. J., Kole, J., Cohn, J. A., Knowlesi, M. R., Silverman, L. M. and Ryszard Kole (1999). Correction of Aberrant Splicing of the Cystic Fibrosis Transmembrane Conductance Regulator (CFTR) Gene by Anti-sense Oligonucleotides. THE JOURNAL OF BIOLOGICAL CHEMISTRY, Vol. 274(51), 36193-36199

Gebski, B. L., Mann, C. J., Fletcher, S., & Wilton, S. D. (2003). Morpholino anti-sense oligonucleotide induced dystrophin exon 23 skipping in mdx mouse muscle. Human molecular genetics, 12(15), 1801-11.

Goemans, N. M., Tulinius, M., van den Akker, J. T., Burm, B. E., Ekhart, P. F., Heuvelmans, N., Holling, T., et al. (2011). Systemic administration of PRO051 in Duchenne's muscular dystrophy. The New England journal of medicine, 364(16), 1513-22. doi:10.1056/NEJMoa1011367

Goyenvalle, A., Babbs, A., Powell, D., Kole, R., Fletcher, S., Wilton, S. D., & Davies, K. E. (2010). Prevention of dystrophic pathology in severely affected dystrophin/utrophin-deficient mice by morpholino-oligomer-mediated exonskipping. Molecular therapy: the journal of the American Society of Gene Therapy, 18(1), 198-205. doi: 10.1038/mt.2009.248

Groman J. D. et al., (2004). Variation in a Repeat Sequence Determines Whether a Common Variant of the Cystic Fibrosis Transmembrane Conductance Regulator Gene Is Pathogenic or Benign. Am. J. Hum. Genet., Vol. 74:176-179

Hefferon T. W., Groman J. D., Yurk C. E., and Cutting G. R. (2004). A variable dinucleotide repeat in the CFTR gene contributes to phenotype diversity by forming RNA secondary structures that alter splicing. PNAS, Vol. 101(10), 3504-3509

Hua, Y., Sahashi, K., Hung, G., Rigo, F., Passini, M. A., Bennett, C. F., & Krainer, A. R. (2010). Anti-sense correction of SMN2 splicing in the CNS rescues necrosis in a type III SMA mouse model. Genes & development, 24(15), 1634-44. doi:10.1101/gad.1941310

Kerem E., Nissim-Rafinia M., Argaman Z., Augarten A., Bentur L., Klar A., Yahav Y., Szeinberg A., Hiba O., Branski D., Corey M., and Kerem B. (1997). A Missense Cystic Fibrosis Transmembrane Conductance Regulator Mutation With Variable Phenotype. Pediatrics, Vol. 100 (3), 1-6

Kerem, B. S (1990). Identification of mutations in regions corresponding to the two putative nucleotide (ATP)-binding folds of the cystic fibrosis gene. Proceedings of the National Academy of Sciences of the United States of America, Vol. 87(21), 8447-8451

Kiesewetter S., Macek M., Davis C., Curristin S. M., Chu C. S., Graham C., Shrimpton A. E., Cashman S. M., Tsui L. C., Mickle J., Amos J., Highsmith W. E., Shuber A., Witt D. R., Crystal R. G. and Cutting G. R. (1993). A mutation in CFTR produces different phenotypes depending on chromosomal background. Nature Genetics, Vol. 5, 274-278. doi:10.1038/ng1193-274

Kinali, M., Arechavala-Gomeza, V., Feng, L., Cirak, S., Hunt, D., Adkin, C., Guglieri, M., et al. (2009). Local restoration of dystrophin expression with the morpholino oligomer AVI-4658 in Duchenne muscular dystrophy: a single-blind, placebocontrolled, dose-escalation, proof-of-concept study. Lancet neurology, 8(10), 918-28. doi: 10.1016/S1474-4422(09)70211-X Lorson, C. L., Rindt, H., & Shababi, M. (2010). Spinal muscular atrophy: mechanisms and therapeutic strategies. Human molecular genetics, 19(R1), R111-8. doi:10.1093/hmg/ddq147

Lu Q. L., Yokota T., Takeda S., Garcia L., Muntoni F. and Partridge T. (2011). The Status of Exon Skipping as a Therapeutic Approach to Duchenne Muscular Dystrophy. Molecular Therapy, Vol. 19(1), 9-15

Mann, C. J., Honeyman, K., Cheng, A. J., Ly, T., Lloyd, F., Fletcher, S., Morgan, J. E., et al. (2001). Anti-sense-induced exon skipping and synthesis of dystrophin in the mdx mouse. Proceedings of the National Academy of Sciences of the United States of America, 98(1), 42-7. doi:10.1073/pnas.011408598

Mendell J. R., Rodino-Klapac L. R., Sahenk Z., Roush K., Bird L., Lowes L. P., Alfano L., Gomez A. M., Lewis S., Kota J., Malik V., Shontz K., Walker C. M., Flanigan K. M., Corridore M., Kean J. R., Allen H. D., Shilling C., Melia K. R., Sazani P., Saoud J. B., Kaye E. M.; the Eteplirsen Study Group (2013). Eteplirsen for the treatment of Duchenne muscular dystrophy. Ann Neurol. 2013 Aug. 1.

Mitrpant, C., Adams, A. M., Meloni, P. L., Muntoni, F., Fletcher, S., & Wilton, S. D. (2009). Rational design of anti-sense oligomers to induce dystrophin exon skipping. Molecular therapy: the journal of the American Society of Gene Therapy, 17(8), 1418-26. doi:10.1038/mt.2009.49

Porensky, P. N., Mitrpant, C., McGovern, V. L., Bevan, A. K., Foust, K. D., Kaspar, B. K., Wilton, S. D., et al. (2012). A single administration of morpholino anti-sense oligomer rescues spinal muscular atrophy in mouse. Human molecular genetics, 21(7), 1625-38. doi:10.1093/hmg/ddr600

Rogan M. P., Stoltz D. A. and Hornick D. B. (2011). Cystic Fibrosis Transmembrane Conductance Regulator Intracellular Processing, Trafficking, and Opportunities for Mutation-Specific Treatment. CHEST, Vol. 139(6), 1480-1490. doi:10.1378/chest.10-2077

Singh, N. N., Shishimorova, M., Cao, L. C., Gangwani, L., & Singh, R. N. (2009). A short anti-sense oligonucleotide masking a unique intronic motif prevents skipping of a critical exon in spinal muscular atrophy. RNA biology, 6(3), 341-50.

Williams, J. H., Schray, R. C., Patterson, C. A., Ayitey, S. O., Tallent, M. K., & Lutz, G. J. (2009). Oligonucleotide-mediated survival of motor neuron protein expression in CNS improves phenotype in a mouse model of spinal muscular atrophy. The Journal of neuroscience: the official journal of the Society for Neuroscience, 29(24), 7633-8. doi:10.1523/JNEUROSCI.0950-09.2009 van Deutekom, J. C., Janson, A. A., Ginjaar, I. B., Frankhuizen, W. S., Aartsma-Rus, A., Bremmer-Bout, M., den Dunnen, J. T., et al. (2007). Local dystrophin restoration with anti-sense oligonucleotide PRO0051. The New England journal of medicine, 357(26), 2677-86. doi:10.1056/NEJMoa073108

The invention claimed is:

1. A method for improving at least one clinical parameter of Cystic Fibrosis in a patient in need thereof, the method comprising administering a therapeutically effective amount of a synthetic polynucleotide molecule to said patient,
   wherein the synthetic polynucleotide molecule comprises a nucleotide sequence having a sequence of at least 18 consecutive nucleotide bases,
   wherein said synthetic polynucleotide molecule binds to a pre-messenger RNA (pre-mRNA) transcript of the Cystic Fibrosis Trans-membrane conductance Regulator (CFTR) gene and suppresses exon 10 exclusion from the mature CFTR mRNA, and
   wherein said nucleotide sequence is complementary to the nucleotide sequence set forth in SEQ ID NO: 2, or to a fragment thereof.

2. The method of claim 1, wherein said clinical parameter is selected from the group consisting of lung function, time to the first pulmonary exacerbation, change in weight, change in height, a change in Body Mass Index (BMI), change in the concentration of sweat chloride, number and/or duration of pulmonary exacerbations, total number of days of hospitalization for pulmonary exacerbations, and the need for antibiotic therapy for sinopulmonary signs or symptoms.

3. The method of claim 1, further comprising the step of administering at least one additional anti-Cystic-Fibrosis agent to said patient.

4. The method of claim 3, wherein said additional anti-Cystic-Fibrosis agent is selected from the group consisting of a CFTR-splicing-modulating agent, a CFTR potentiator and a CFTR corrector.

5. The method of claim 4, wherein said CFTR-splicing-modulating agent is a synthetic polynucleotide molecule configured to suppress intron 22 cryptic exon inclusion in the mature CFTR mRNA; said CFTR potentiator is
   N-(2,4-Di-tert-butyl-5-hydroxyphenyl)-4-oxo-1,4-dihydroquinoline-3-carboxamide (Ivacaftor); or said CFTR corrector is selected from the group consisting of
   3-[5-(2-fluorophenyl)-1,2,4-oxadiazol-3-yl]benzoic acid (Ataluren) and
   3-{6-{[1-(2,2-difluoro-1,3-benzodioxol-5-yl)cyclopropanecarbonyl]amino}-3-methylpyridin-2-yl}benzoic acid (Lumacaftor).

6. The method of claim 1, wherein said step of administering involves oral, nasal, aerosol, inhalational, abdominal, subcutaneous, intra-peritoneal or intravenous administration.

7. A method for modulation of splicing of a CFTR pre-mRNA, the method comprising administering, to a patient in need thereof, a synthetic polynucleotide molecule comprising a nucleotide sequence having a sequence of at least 18 consecutive nucleotide bases,
- wherein said synthetic polynucleotide molecule binds to a pre-messenger RNA (pre-mRNA) transcript of the Cystic Fibrosis Trans-membrane conductance Regulator (CFTR) gene and suppresses exon 10 exclusion from the mature CFTR mRNA, and
- wherein said nucleotide sequence is complementary to the nucleotide sequence set forth in SEQ ID NO: 2, or to a fragment thereof.

8. A method for reducing the level of an mRNA molecule comprising the nucleotide sequence set forth in SEQ ID NO: 12, the method comprising administering, to a patient in need thereof, a synthetic polynucleotide molecule, comprising a nucleotide sequence having a sequence of at least 18 consecutive nucleotide bases,
- wherein said synthetic polynucleotide molecule binds to a pre-messenger RNA (pre-mRNA) transcript of the Cystic Fibrosis Trans-membrane conductance Regulator (CFTR) gene and suppresses exon 10 exclusion from the mature CFTR mRNA, and
- wherein said nucleotide sequence is complementary to the nucleotide sequence set forth in SEQ ID NO: 2, or to a fragment thereof.

9. A method for increasing the level of an mRNA molecule comprising the nucleotide sequence set forth in SEQ ID NO: 1, the method comprising administering to a patient in need thereof, a synthetic polynucleotide molecule, comprising a nucleotide sequence having a sequence of at least 18 consecutive nucleotide bases,
- wherein said synthetic polynucleotide molecule binds to a pre-messenger RNA (pre-mRNA) transcript of the Cystic Fibrosis Trans-membrane conductance Regulator (CFTR) gene and suppresses exon 10 exclusion from the mature CFTR mRNA, and
- wherein said nucleotide sequence is complementary to the nucleotide sequence set forth in SEQ ID NO: 2, or to a fragment thereof.

* * * * *

SEQUENCE LISTING

```
<160> NUMBER OF SEQ ID NOS: 28

<210> SEQ ID NO 1
<211> LENGTH: 6132
<212> TYPE: RNA
<213> ORGANISM: Homo sapiens

<400> SEQUENCE: 1
aauuggaagc aaaugacauc acagcagguc agagaaaaag gguugagcgg caggcaccca      60
gaguaguagg ucuuuggcau uaggagcuug agcccagacg gcccuagcag ggaccccagc     120
gcccgagaga ccaugcagag gucgccucug gaaaaggcca gcguugucuc caaacuuuuu     180
uucagcugga ccagaccaau uuugaggaaa ggauacagac agcgccugga auugucagac     240
auauaccaaa uccccuucugu ugauucugcu gacaaucuau cugaaaaauu ggaaagagaa     300
ugggauagag agcuggcuuc aaagaaaaau ccuaaacuca uuaaugcccu ucggcgaugu     360
uuuuucugga gauuuauguu cuauggaauc uuuuuuauauu uaggggaagu caccaaagca     420
guacagccuc ucuuacuggg aagaaucaua gcuuccuaug acccggauaa caaggaggaa     480
cgcucuaucg cgauuuaucu aggcauaggc uuaugccuuc ucuuuauugu gaggacacug     540
cuccuacacc cagccauuuu uggccuucau cacauuggaa ugcagaugag aauagcuaug     600
uuuaguuuga uuuauaagaa gacuuuaaag cugucaagcc guguucuaga uaaaauaagu     660
auuggacaac uuguuagucu ccuuuccaac aaccugaaca aauuugauga aggacuugca     720
uuggcacauu ucgugggau cgcuccuuug caaguggcac uccucauggg gcuaaucugg     780
gaguuguuac aggcgucugc cuucugugga cuggguuucc ugauaguccu ugcccuuuuu    840
caggcugggc uagggagaau gaugaugaag uacagagauc agagagcugg gaagaucagu    900
gaaagacuug ugauuaccuc agaaaugauu gaaaauaucc aaucuguuaa ggcauacugc    960
ugggaagaag caauggaaaa aaugauugaa acuuaagac aaacagaacu gaaacugacu   1020
cggaaggcag ccuaugugag auacuucaau agcuucagccu ucuucuucuc aggguucuuu   1080
guggugguuu uaucugugcu ucccuaugca cuaaucaaag gaaucauccc ccggaaaaua   1140
uucaccacca ucucauucug cauuguucug cgcauggcgg ucacucggca auuucccugg   1200
gcuguacaaa cauggauga cucucuugga gcaauaaaca aaauacagga uucuuacaa   1260 aagcaagaau auaagacauu ggaauauaac uuaacgacua cagaaguagu gauggagaau   1320
guaacagccu ucugggagga gggauuuggg aauuauuug agaaagcaaa acaaaacaau   1380
aacaauagaa aaacuucuaa ugguugauac gccucuucu ucaguaauuu cucacuucuu   1440
gguacuccug uccugaaaga uauuaauuuc aagauagaaa gaggacaguu guuggcgguu   1500 gcuggauca cuggagcagg caagacuuca cuucuaaugg ugauuauggg agaacuggag   1560
ccuucagagg guaaaauuaa gcacagugga agaauuucau ucuguucuca guuuuccugg   1620
auuaugccug gcaccauuaa agaaauauc aucuuugguguu uuccuauga ugaauauaga   1680 uacagaagcg ucaucaaagc augccaacua gaagaggaca cuccaaguu ugcagagaaa   1740 gacaauauag uucuuggaga agguggaauc acacugagug gaggucaacg agcaagaauu   1800
ucuuuagcaa gagcaguaua caaagaugcu gauuuguauu uauuagacuc uccuuuugga   1860
uaccuagaug uuuuaacaga aaaagaaaua uuugaaagcu gugucuguaa acugauggcu   1920
```

```
aacaaaacua ggauuuuggu cacuucuaaa auggaacauu uaaagaaagc ugacaaaaua    1980
uuaauuuugc augaagguag cagcuauuuu uaugggacau uuucagaacu ccaaaaucua    2040
cagccagacu uuagcucaaa acucauggga ugugauucuu ucgaccaauu uagugcagaa    2100
agaagaaauu caauccuaac ugagaccuua caccguuucu cauuagaagg agaugcuccu    2160
gucuccugga cagaaacaaa aaaacaaucu uuuaaacaga cuggagaguu uggggaaaaa    2220
aggaagaauu cuauucucaa uccaaucaac ucuauacgaa aauuuccau ugugcaaaag     2280
acucccuuac aaaugaaugg caucgaagag gauucugaug agccuuuaga gagaaggcug    2340
uccuuaguac cagauucuga gcagggagag gcgauacugc cucgcaucag cgugaucagc    2400
acuggcccca cgcuucaggc acgaaggagg cagucugucc ugaaccugau gacacacuca    2460
guuaaccaag gucagaacau ucaccgaaag acaacagcau ccacacgaaa agugucacug    2520
gccccucagg caaacuugac ugaacuggau auauauucaa gaagguuauc ucaagaaacu    2580
ggcuuggaaa uagugaaga auuaacgaa gaagacuuaa aggagugcuu uuuugaugau      2640
auggagagca uaccagcagu gacuacaugg aacacauacc uucgauauau uacuguccac    2700
aagagcuuaa uuuuugugcu aauuggugc uaguaauuu ucuggcaga gguggcugcu       2760
ucuuugguug ugcuguggcu ccuuggaaac acuccucuuc aagacaaagg gaauaguacu    2820
cauaguagaa auaacagcua ugcagugauu ucaccagca ccaguucgua uuauguguuu     2880
uacauuuacg ugggaguagc cgacacuuug cuugcuaugg gauucuucag aggcuacca     2940
cuggugcaua ucuaaucac agugucgaaa auuuuacacc acaaaauguu acauucuguu     3000
cuucaagcac cuaugucaac cccuaacacg ugaaagcag gugggauucu uaauagauuc     3060
uccaaagaua uagcaauuuu ggaugaccuu cugccucuua ccauauuuga cuucauccag    3120
uuguuauuaa uugugauugg agcuauagca guugucgcag uuuuacaacc cuacaucuuu    3180
guugcaacag ugccagugau aguggcuuuu auuauguuga gagcauauuu ccuccaaaacc   3240
ucacagcaac ucaaacaacu ggaaucgaaa ggcaggaguc caauuuucac ucaucuguu     3300
acaagcuuaa aaggacuaug gacacuucgu gccuucggac ggcagccuua cuuugaaacu    3360
cuguccaca aagcucugaa uuuacauacu gccaacuggu ucuuguaccu gucaacacug     3420
cgcugguucc aaaugagaau agaaaugauu uuugucaucu ucuucauugc uguuaccuuc    3480
auuccauuu uaacaacagg agaaggagaa ggaagaguug uauuauccu gacuuuagcc      3540
augaauauca ugaguacauu gcagugggcu guaaacucca gcauagaugu ggauagcuug    3600
augcgaucug ugagccgagu cuuuaaguuc auugacaugc caacagaagg uaaaccuacc    3660
aagucaaccaa aaccauacaa gaauggccaa cucucgaaag uuaugauuau ugagaauuca    3720
cacgugaaga aagaugacau cuggcccuca gggggccaaa ugacugucaa agaucucaca    3780
gcaaaauaca cagaaggugg aaaugccaua uuagagaaca uuccuucuc aauaagaccu     3840
ggccagaggg ugggcucucu gggaagaacu ggaucaggga agaguacuuu guuaucagcu    3900
uuuugagac uacugaacac ugaaggagaa auccagaucg augguguguc uugggauuca     3960
auaacuuugc aacaguggag gaaagccuuu ggagugauac cacagaaagu auuuauuuuu    4020
ucuggaacau uuagaaaaaa cuggaucccu uaugaacagu ggagugauca agaaauaugg   4080
aaaguugcag augagguugg cucagaucu ugauagaac aguuccugg gaagcuugac      4140
uuugccuug uggauggggg cuguguccua agccauggcc acaagcaguu gaugugcuug    4200
gcuagaucug uucucaguaa ggcgaagauc uugcugcuug augaacccag ugcucauugg   4260
gauccaguaa cauaccaaau aauuagaaga acucuaaaac aagcauuugc ugauugcaca    4320
```

| | | | | | |
|---|---|---|---|---|---|
| guaauucucu | gugaacacag | gauagaagca | augcuggaau | gccaacaauu | uuuggucaua | 4380 |
| gaagagaaca | aagugcggca | guacgauucc | auccagaaac | ugcugaacga | gaggagccuc | 4440 |
| uuccggcaag | ccaucagccc | cuccgacagg | gugaagcucu | uccccaccg | gaacucaagc | 4500 |
| aagugcaagu | cuaagcccca | gauugcugcu | cugaaagagg | agacagaaga | agaggugcaa | 4560 |
| gauacaaggc | uuuagagagc | agcauaaaug | uugacauggg | acauuugcuc | auggaauugg | 4620 |
| agcucguggg | acagucaccu | cauggaauug | gagcucgugg | aacaguuacc | ucugccucag | 4680 |
| aaaacaagga | ugaauuaagu | uuuuuuuuaa | aaagaaaca | uuuggaagg | ggaauugagg | 4740 |
| acacugauau | ggguucuugau | aaauggcuuc | ucggcaauag | ucaaauugug | ugaaaggguac | 4800 |
| uucaaauccu | ugaagauuua | ccacuugugu | uuugcaagcc | agauuuuccu | gaaaacccuu | 4860 |
| gccaugugcu | aguaauugga | aaggcagcuc | uaaaugucaa | ucagccuagu | ugaucagcuu | 4920 |
| auugucuagu | gaaacucguu | aauuuguagu | guuggagaag | aacugaaauc | auacuucuua | 4980 |
| ggguuaugau | uaaguaauga | uaacuggaaa | cuucagcggu | uuauauaagc | uuguauuccu | 5040 |
| uuuucucucc | ucuccccaug | auguuuagaa | acacaacuau | auuguuugcu | aagcauucca | 5100 |
| acuaucucau | uuccaagcaa | guauuagaau | accacaggaa | ccacaagacu | gcacaucaaa | 5160 |
| auaugcccca | uucaacaucu | agugagcagu | caggaaagag | aacuuccaga | uccuggaaau | 5220 |
| cagggguuagu | auuguccagg | ucuaccaaaa | aucucaauau | uucagauaau | cacaauacau | 5280 |
| cccuuaccug | ggaaagggcu | guuauaaucu | uucacagggg | acaggauggu | ucccuugaug | 5340 |
| aagaaguuga | uaugccuuuu | cccaacucca | gaaagugaca | agcucacaga | ccuuugaacu | 5400 |
| agaguuuagc | uggaaaagua | uguuagugca | aauugucaca | ggacagcccu | ucuuuccaca | 5460 |
| gaagcuccag | guagggguug | uguaaguaga | uaggccaugg | gcacuguggg | uagacacaca | 5520 |
| ugaaguccaa | gcauuuagau | guauagguug | augguggaa | guuucaggc | uagauguaug | 5580 |
| uacuucaugc | ugucuacacu | aagagagaau | gagagacaca | cugaagaagc | accaaucaug | 5640 |
| aauuaguuuu | auaugcuucu | guuuauaau | uuugugaagc | aaaauuuuuu | ucuaggaaa | 5700 |
| uauuuauuuu | aauaaugu | caaacauaua | uaacaaugcu | guauuuuaaa | agaaugauua | 5760 |
| ugaauuacau | uuguauaaaa | uaauuuuuau | auuugaauua | uugacuuuuu | auggcacuag | 5820 |
| uauuucuaug | aaaauauuaug | uuaaaacugg | gacagggggag | aaccuagggu | gauauuaacc | 5880 |
| aggggccaug | aaucaccuuu | uggucuggag | ggaagccuug | gggcugaugc | aguuguugcc | 5940 |
| cacagcugua | ugauucccag | ccagcacagc | cucuuagaug | caguucugaa | gaagauggua | 6000 |
| ccaccagucu | gacuguuucc | aucaagggua | cacgccuuc | ucaauccaa | acugacucuu | 6060 |
| aagaagacug | cauuauauuu | auuacuguaa | gaaaauauca | cuugucaaua | aaauccauac | 6120 |
| auuugugugua | aa | | | | | 6132 |

<210> SEQ ID NO 2
<211> LENGTH: 983
<212> TYPE: RNA
<213> ORGANISM: Homo sapiens

<400> SEQUENCE: 2

| | | | | | |
|---|---|---|---|---|---|
| cagcuuugaa | agaggaggau | uauaaaaucu | aucucauguu | aaugcugaag | auuaaauaau | 60 |
| aguguuuaug | uaccccgcuu | auaggagaag | aggguguguga | uguguguguu | uguguguguu | 120 |
| uguguauguuu | uauguauaca | uguauguauu | cagucuuuac | ugaaauuaaa | aaaucuuuaa | 180 |
| cuugauaaug | ggcaaauauc | uuaguuuuag | aucauguccu | cuagaaaccg | uaugcuauau | 240 |

```
aauuauguac uauaaaguaa uaauguauac aguguaaugg aucaugggcc augugcuuuu    300
caaacuaauu guacauaaaa caagcaucua uugaaaauau cugacaaacu caucuuuuau    360
uuuugaugug ugugugugug ugugugguu uuuuaacag ggauuugggg aauuauuuga      420
```

```
<210> SEQ ID NO 7
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 7
cuuguggucu ccagaaauca agaug                                          25

<210> SEQ ID NO 8
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 8
aacagaugga agacucuugu aauua                                          25

<210> SEQ ID NO 9
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 9
ucaggguguc uuacucacca uuuua                                          25

<210> SEQ ID NO 10
<211> LENGTH: 22
<212> TYPE: RNA
<213> ORGANISM: Artificial Sequence
<220> FEATURE:
<223> OTHER INFORMATION: Antisense Oligonucleotide

<400> SEQUENCE: 10
cuagaaaaaa aaagagacau gg                                             22

<210> SEQ ID NO 11
<211> LENGTH: 6216
<212> TYPE: RNA
<213> ORGANISM: Homo sapiens

<400> SEQUENCE: 11
aauuggaagc aaaugacauc acagcagguc agagaaaaag gguugagcgg caggcaccca    60
gaguaguagg ucuuuggcau uaggagcuug agcccagacg gcccuagcag ggaccccagc   120
gcccgagaga ccaugcagag gucgccucug gaaaaggcca gcguugucuc caaacuuuuu   180
uucagcugga ccagaccaau uuugaggaaa ggauacagag agcgccugga auugucagac   240
auauaccaaa ucccuucugu gauucugcu gacaaucuau cugaaaaauu ggaaagagaa   300
ugggauagag agcuggcuuc aaagaaaaau ccuaaacuca uuaagcccu ucggcgaugu    360 uuuuucugga gauuuauguu cuauggaauc uuuuuauauu uaggggaagu caccaaagca   420
guacagccuc ucuuacuggg aagaaucaua gcuuccuaug acccggauaa caaggaggaa   480
cgcucuaucg cgauuuaucu aggcauaggc uuaugccuuc ucuuuaugu gaggacacug   540 cuccuacacc cagccauuuu uggccuucau cacauuggaa ugcagaugag aauagcuaug   600
uuuaguuuga uuuauaagaa gacuuuaaag cugucaagcc guguucuaga uaaaauaagu   660
auuggacaac uuguuagucu ccuuuccaac aaccugaaca aauuugauga aggacuugca   720
```

| | |
|---|---|
| uuggcacauu cgguguggau cgcuccuuug caagugggcac uccucauggg gcuaaucugg | 780 |
| gaguuguuac aggcgucugc cuucugugga cuugguuucc ugauaguccu ugcccuuuuu | 840 |
| caggcugggc uagggagaau gaugaugaag uacagagauc agagagcugg gaagaucagu | 900 |
| gaaagacuug ugauuaccuc agaaaugauu gaaaauaucc aaucuguuaa ggcauacugc | 960 |
| ugggaagaag caauggaaaa aaugauugaa aacuuaagac aaacagaacu gaaacugacu | 1020 |
| cggaaggcag ccuaugugag uacuucaau agcucagccu ucuucuucuc agggucuuu | 1080 |
| guggguguuu uaucugugcu ucccuaugca cuaaucaaag gaaucauccu ccggaaaaua | 1140 |
| uucaccacca ucucauucug cauuguucug cgcauggcgg ucacucggca auucccugg | 1200 |
| gcuguacaaa cauggguauga cucucuugga gcaauaaaca aaauacagga uuucuuacaa | 1260 |
| aagcaagaau auaagacauu ggaauauaac uuaacgacua cagaaguagu gauggagaau | 1320 |
| guaacagccu ucggggagga gggauuuggg gaauuauuug agaaagcaaa acaaaacaau | 1380 |
| aacaauagaa aaacuucuaa uggugaugac agcccucucu ucaguaauuu cucacuucuu | 1440 |
| gguacuccug uccugaaaga uauuaauuuc aagauagaaa gaggacaguu guuggcgguu | 1500 |
| gcuggaucca cuggagcagg caagacuuca cuucuaaugg ugauuauggg agaacuggag | 1560 |
| ccuucagagg guaaaauuaa gcacagugga agaauuucau ucuguucuca guuuccugg | 1620 |
| auuaugccug gcaccauuaa agaaaauauc aucuuugggu uuccuauga ugaauauaga | 1680 |
| uacagaagcg ucaucaaagc augccaacua gaagaggaca ucuccaaguu ugcagagaaa | 1740 |
| gacaauauag uucuuggaga aggugggaauc acacugagug gaggucaacg agcaagaauu | 1800 |
| ucuuuagcaa gagcaguaua caaagaugcu gauuuguauu uauuagacuc uccuuuugga | 1860 |
| uaccuagaug uuuuaacaga aaagaaaua uuugaaagcu gugucuguaa acugauggcu | 1920 |
| aacaaaacua ggauuuuggu cacuucuaaa augaacauu uaagaaagc ugacaaaaua | 1980 |
| uuaauuuugc augaagguag cagcuauuuu uaugggacau uucagaaacu ccaaaaucua | 2040 |
| cagccagacu uuagcucaaa acucauggga ugugauucuu ucgaccaauu uagugcagaa | 2100 |
| agaagaaauu caauccuaac ugagaccuua caccguuucu cauuagaagg agaugcuccu | 2160 |
| gucuccugga cagaaacaaa aaaacaaucu uuuaaacaga cuggagaguu uggggaaaaa | 2220 |
| aggaagaauu cuauucucaa uccaaucaac ucuauacgaa aauuuccau ugugcaaaag | 2280 |
| acucccuuac aaaugaaugg caucgaagag gauucgaug agccuuuaga gagaaggcug | 2340 |
| uccuuaguac cagauucuga gcaggagag gcgauacugc cucgcaucag cgugaucagc | 2400 |
| acuggcccca cgcuucaggc acgaaggagg cagucugucc ugaaccugau gacacacuca | 2460 |
| guuaaccaag gucagaacau ucaccgaaag acaacagcau ccacacgaaa agugucacug | 2520 |
| gccccucagg caaacuugac ugaacuggau auauauucaa gaagguuauc ucaagaaacu | 2580 |
| ggcuuggaaa uaagugaaga aauuaacgaa gaagacuuaa aggagugcuu uuuugaugau | 2640 |
| auggagagca uaccagcagu gacuacaugg aacacauacc uucgauauau uacguccac | 2700 |
| aagagcuuaa uuuuugugcu aauuuggugc uuaguaauuu ucuggcaga gguggcugcu | 2760 |
| ucuuugguug ugcugugggcu ccuggaaac acuccucuuc aagacaaagg gaauagacu | 2820 |
| cauaguagaa auaacagcua ugcagugauu ucaccagca ccaguucgua uuaguguuu | 2880 |
| uacauuuacg ugggaguagc cgacacuuug cuugcuaugg gauucuucag aggucuacca | 2940 |
| cugguugcauа cucuaaucac agugucgaaa auuuuacacc acaaaauguu acauucuguu | 3000 |
| cuucaagcac cuaugucaac cccucaacacg uugaaagcag gugggauucu uaauagauuc | 3060 |
| uccaaagaua uagcaauuuu ggaugaccuu cugccucuua ccauauuuga cuuucauccag | 3120 |

```
uuguuauuaa uugugauugg agcuauagca guugucgcag uuuuacaacc cuacaucuuu    3180
guugcaacag ugccagugau aguggcuuuu auuauguuga gagcauauuu ccuccaaacc    3240
ucacagcaac ucaaacaacu ggaaucugaa ggcaggaguc caauuuucac ucaucuuguu    3300
acaagcuuaa aaggacuaug gacacuucgu gccuucggac ggcagccuua cuugaaaacu    3360
cuguuccaca aagcucugaa uuuacauacu gccaacuggu ucuuguaccu gucaacacug    3420
cgcugguucc aaaugagaau agaaaugauu uuugucaucu ucuucauugc guuaccuuc     3480
auuuccauuu uaacaacagg agaaggagaa ggaagaguug guauuauccu gacuuuagcc    3540
augaauauca ugaguacauu gcagggggcu guaaaucca gcauagaugu ggauagcuug     3600
augcgaucug ugagccgagu cuuuaaguuc auugacaugc caacagaagg uaaaccuacc    3660
aagucaacca aaccauacaa gaauggccaa cucucgaaag uuaugauuau ugagaauuca    3720
cacgugaaga aagaugacau cuggcccuca gggggccaaa ugacugucaa agaucucaca    3780
gcaaaauaca cagaaggugg aaaugccaua uuagagaaca uuccuucuc aauaagccu      3840
ggccagaggu ugacuuguca ucuugauuuc uggagaccac aagguaauga aaaauaauua    3900
caagagucuu ccaucuguug caguauuaaa auggugggcc ucuugggaag aacuggauca    3960
gggaagagua cuuuguuauc agcuuuuuug agacuacuga acacugaagg agaaauccag    4020
aucgauggug ugucuuggga uucaauaacu ugcaacagu ggaggaaagc cuuuggagug     4080
auaccacaga aaguauuuau uuuucugga acauuuagaa aaaacuugga ucccaugaa      4140
caguggagug aucaagaaau auggaaaguu gcagaugagg uugggcucag aucugugaua    4200
gaacaguuuc cugggaagcu ugacuuuguc cuuguggaug ggggcugugu ccuaagccau    4260
ggccacaagc aguugaugug cuuggcuaga ucuguuucuca guaaggcgaa gaucuugcug   4320
cuugaugaac ccagugcuca uuuggaucca guaacauacc aaauaauuag aagaacucua    4380
aaacaagcau uugcugauug cacaguaauu cucugugaac acaggauaga agcaaugcug    4440
gaaugccaac aauuuuuggu cauagaagag aacaaagugc ggcaguacga uuccauccag    4500
aaacugcuga acgagaggag ccucuuccgg caagccauca gccccuccga cagggugaag    4560
cucuuucccc accggaacuc aagcaagugc aagucaagc cccagauugc ugcucugaaa     4620
gaggagacag aagaagaggu gcaagauaca aggcuuuaga gagcagcaua aauguugaca    4680
ugggacauuu gcucauggaa uuggagcucg ugggacaguc accucaugga auuggagcuc    4740
guggaacagu uaccucugcc ucagaaaaca aggaugaauu aaguuuuuuu uuaaaaaaga    4800
aacauuuggu aagggaauu gaggacacug auaugggucu ugauaaaugg cuccuggca      4860
auagucaaau uguguaaag guacuucaaa uccuugaaga uuuaccacuu uguuuugca      4920
agccagauuu uccugaaaac ccuugccaug ugcuaguaau uggaaaggca gcucuaaaug    4980
ucaaucagcc uaguugauca gcuuauuguc uagugaaacu cguuaauuug uaguguugga    5040
gaagaacuga aaucuacuu cuuagggua ugauuaagua augauaacug gaaacuucag      5100
cgguuuauau aagcuuguau uccuuuuucu cuccucuccc caugauguuu agaaacacaa    5160
cuauauuguu ugcuaagcau uccaacuauc ucauuuccaa gcaaguauua gaauaccaca    5220
ggaaccacaa gacugcacau caaaauaugc cccauucaac aucagugag cagucaggaa     5280
agagaacuuc cagauccugg aaaucagggu uaguauuguc caggucuacc aaaaaucuca    5340
auauuucaga uaaucacaau acaucccuua ccugggaaag ggcuguuaua aucuuucaca    5400
ggggacagga ugguucccuu gaugaagaag uugauaugcc uuuucccaac uccagaaagu    5460
```

```
gacaagcuca cagaccuuug aacuagaguu uagcuggaaa aguauguuag ugcaaauugu    5520
cacaggacag cccuucuuuc cacagaagcu ccagguagag ggugaguaag uagauaggcc    5580
augggcacug ugggauagaca cacaugaagu ccaagcauuu agauguauag guugauggug    5640
guauguuuuc aggcuagaug uauguacuuc augcugucua cacuaagaga gaaugagaga    5700
cacacugaag aagcaccaau caugaauuag uuuuauaugc uucuguuuua uaauuuugug    5760
aagcaaaauu uuucucuag gaaauauuua uuuuaauaau guucaaaca uauauaacaa    5820 ugcuguauuu uaaaagaaug auuaugaauu acauuguau aaaauaauuu uuauauuuga    5880
aauauugacu uuuuauggca cuaguauuuc uaugaaauau uauguuaaaa cuggacagg    5940 ggagaaccua ggguugauauu aaccagggc cauaaucac cuuuggucu ggagggaagc    6000 cuuggggcug augcaguugu ugcccacagc uguaugauuc ccagccagca cagcccucuua    6060 gaugcaguuc ugaagaagau gguaccacca gucugacugu uccaucaag gguacacugc    6120 cuucucaacu ccaaacugac ucuuaagaag acugcauuau auuuauuacu guaagaaaau    6180
aucacuuguc aauaaaaucc auacauuugu gugaaa                              6216

<210> SEQ ID NO 12
<211> LENGTH: 5949
<212> TYPE: RNA
<213> ORGANISM: Homo sapiens

<400> SEQUENCE: 12
aauuggaagc aaaugacauc acagcagguc agagaaaaag gguugagcgg caggcaccca      60
gaguaguagg ucuuuggcau uaggagcuug agcccagacg gcccuagcag ggaccccagc     120
gcccgagaga ccaugcagag gucgccucug gaaaaggcca gcguugucuc caaacuuuuu     180
uucagcugga ccagaccaau uuugaggaaa ggauacagac agcgccugga auugucagac     240
auauaccaaa ucccuucugu ugauucugcu gacaaucuau cugaaaaauu ggaaagagaa     300
ugggauagag agcuggcuuc aaagaaaaau ccuaaacuca uuaaugcccu ucggcgaugu     360 uuuucugga gauuuauguu cuauggaauc uuuuuauauu uaggggaagu caccaaagca     420
guacagccuc ucuuacuggg aagaaucaua gcuuccuaug acccggauaa caaggaggaa     480
cgcucuaucg cgauuuaucu aggcauaggc uuaugccuuc ucuuuauugu gaggacacug     540
cuccuacacc cagccauuuu uggccuucau cacauuggaa ugcagaugag aauagcuaug     600
uuuaguuuga uuuauaagaa gacuuuaaag cugucaagcc guguucuaga uaaaauaagu     660
auuggacaac uuguuagucu ccuuuccaac aaccugaaca aauuugauga aggacuugca     720
uuggcacauu ucguguggau cgcuccuuug caaguggcac uccucaugg gcuaaucugg     780 gaguuguuac aggcgucugc cuucuggga cuugguuucc ugauaguccu ugcccuuuuu     840
caggcugggc uagggagaau gaugaugaag uacagagauc agagagcugg gaagaucagu     900
gaaagacuug ugauuaccuc agaaaugauu gaaauauccc aaucguuaa ggcauacugc     960 ugggaagaag caauggaaaa aaugauugaa aacuuaagac aaacagaacu gaaacugacu    1020
cggaaggcag ccuaugugag auacuucaau agcucagccu ucuucuucuc aggguucuuu    1080
gugguguuuu uaucgugcu ucccuaugca cuaucaaag gaaucauccu ccggaaaaua    1140
uucaccacca ucucauucug cauuguucug cgcauggcgg ucacucggca auuucccugg    1200
gcuguacaaa cauggauga cucucuugga gcauaaaaca aaauacagga uucuuacaa    1260 aagcaagaau auaagacauu ggaauauaac uuaacgacua cagaaguagu gauggagaau    1320
guaacagccu ucugggagga gacuucacuu cuaauggugu auugggagga acuggagccu    1380
```

```
ucagagggua aaauuaagca caguggaaga auuucauucu guucucaguu uccuggauu    1440
augccuggca ccauuaaaga aaauaucauc uuugguguuu ccuaugauga auauagauac   1500
agaagcguca ucaaagcaug ccaacuagaa gaggacaucu ccaaguuugc agagaaagac   1560
aauauaguuc uuggagaagg uggaaucaca cugagguggag ucaacgagc aagaauuucu   1620
uuagcaagag caguauacaa agaugcugau uguauuuau uagacucucc uuuuggauac    1680
cuagauguuu uaacagaaaa agaaauauuu gaaagcugug ucuguaaacu gauggcuaac   1740
aaaacuagga uuuuggucac uucuaaaaug gaacauuuaa agaaagcuga caaaauauua   1800
auuuugcaug aagguagcag cuauuuuuau gggacauuuu cagaacucca aaaucuacag   1860
ccagacuuua gcucaaaacu caugggaugu gauucuuucg accauuuuag ugcagaaaga   1920
agaaauucaa uccuaacuga gaccuuacac cguuucucau uagaaggaga ugcuccuguc   1980
uccuggacag aaacaaaaaa acaaucuuuu aaacagacug gagaguuugg ggaaaaaagg   2040
aagaauucua uucucaaucc aaucaacucu auacgaaaau uuccauugu gcaaaagacu    2100
cccuuacaaa ugaauggcau cgaagaggau ucgaugagc cuuagagag aaggcuguuc    2160
uuaguaccag auucugagca gggagaggcg auacugccuc gcaucagcgu gaucagcacu   2220
ggccccacgc uucaggcacg aaggaggcag ucuguccuga accgaugac acacucaguu    2280
aaccaagguc agaacauuca ccgaaagaca acagcaucca cacgaaaagu gucacuggcc   2340
ccucaggcaa acuugacuga acuggauaua uauucaagaa gguuaucuca agaaacuggc   2400
uuggaaauaa gugaagaaau uaacgaagaa gacuuuaagg agugcuuuuu ugaugauaug   2460
gagagcauac cagcagugac uacauggaac acauaccuuc gauauauuac uguccacaag   2520
agcuuaauuu uugugcuaau uggugcuuua guauuuuuc uggcagaggu ggcugcuucu    2580
uugguugugc uguggcuccu uggaaacacu ccucuucaag acaaagggaa uaguacucau   2640
aguagaaaua acagcuaugc agugauuauc accagcacca guucguauua uguguuuuac   2700
auuuacgugg gaguagccga cacuuugcuu gcuaugggau cuucagagg ucuaccacug   2760
gugcauacuc uaaucacagu gucgaaaauu uuacaccaca aaauguuaca uucguucuu    2820
caagcaccua ugucaacccu caacacguug aaagcaggug ggauucuuaa uagauucucc   2880
aaagauauag caauuuugga ugaccuucug ccucuuacca uauugacuu cauccaguug    2940
uuauuaauug ugauuggagc uauagcaguu gucgcaguuu acaacccuua caucuuugu    3000
gcaacagugc cagugauagu ggcuuuuauu auguugagag cauauuuccu ccaaaccuca   3060
cagcaacuca aacaacugga aucgaaggc aggageccaa uuucacuca ucuuguuaca    3120
agcuuaaaag gacuauggac acuucgugcc uucggacggc agccuuacuu ugaaacucug   3180
uuccacaaag cucugaauuu acauacgccc aacugguucu guaccuguc aacacugcgc   3240
ugguccaaaa ugagaauaga aaugauuuuu gucaucuucu cauugcugu uaccuucauu    3300
uccauuuuaa caacaggaga aggagaagga agaguuggua uuaaccugac uuuagccaug   3360
aauaucauga guacauugca gugggcugua aacuccagca uagaugugga uagcuugaug   3420
cgaucuguga gccgagucuu uaaguucauu gacaugccaa cagaagguaa accuaccaag   3480
ucaaccaaac cauacaagaa uggccaacuc ucgaaaguua ugauuauuga gaauucacac   3540
gugaagaaag augacaucug gcccucaggg ggccaaauga cugucaaaga ucucacagca   3600
aaauacacag aagguggaaa ugccauauua gagaacauuu ccuucucaau aagucuggc    3660
cagagggugg gccucuuggg aagaacugga ucagggaaga guacuuuguu aucagcuuuu   3720
```

| | |
|---|---|
| uugagacuac ugaacacuga aggagaaauc cagaucgaug ugugucuug ggauucaaua | 3780 |
| acuuugcaac aguggaggaa agccuuugga gugauaccac agaaaguauu uauuuuuucu | 3840 |
| ggaacauuua gaaaaaacuu ggaucccuauu gaacagugga gugaucaaga aauauggaaa | 3900 |
| guugcagaug agguugggcu cagaucugug auagaacagu uccugggaa gcuugacuuu | 3960 |
| guccuugugg auggggggcug uguccuaagc cauggccaca agcaguugau gugcuuggcu | 4020 |
| agaucuguuc ucaguaaggc gaagaucuug cugcuugaug aacccagugc ucauuuggau | 4080 |
| ccaguaacau accaaauaau uagaagaacu cuaaacaag cauuugcuga uugcacagua | 4140 |
| auucucugug aacacaggau agaagcaaug cuggaaugcc aacaauuuuu ggucauagaa | 4200 |
| gagaacaaag ugcggcagua cgauuccauc cagaaacugc ugaacgagag gagccucuuc | 4260 |
| cggcaagcca ucagcccuc cgacaggug aagcucuuuc cccaccggaa cucaagcaag | 4320 |
| ugcaagucua agccccagau ugcugcucug aaagaggaga cagaagaaga ggugcaagau | 4380 |
| acaaggcuuu agagagcagc auaaauguug acauggaca uuugcucaug gaauuggagc | 4440 |
| ucgugggaca gucaccucau ggaauuggag cucguggaac aguuaccucu gcccagaaaa | 4500 |
| acaaggauga auuaaguuuu uuuuuaaaaa agaaacauuu gguaagggga auugaggaca | 4560 |
| cugauauggg ucuugauaaa uggcuuccug gcaauaguca aauugugga aagguacuuc | 4620 |
| aaauccuuga agauuuacca cuuguguuuu gcaagccaga uuuuccugaa aacccuugcc | 4680 |
| augcuagu aauggaaag gcagcucuaa augucaauca gccuaguuga ucagcuuauu | 4740 |
| gucuagugaa acucguuaau uguagugu ggagaagaac ugaaaucaua cuucuuaggg | 4800 |
| uuaugauuaa guaaugauaa cuggaaacuu cagcgguuua uauaagcuug uauuccuuuu | 4860 |
| ucucuccucu ccccaugaug uuuagaaaca caacuauauu guuugcuaag cauuccaacu | 4920 |
| aucucauuuc caagcaagua uuagaauacc acaggaacca caagacugca caucaaaaua | 4980 |
| ugccccauuc aacaucuagu gagcagucag gaaagagaac uuccagaucc uggaaaucag | 5040 |
| gguuaguauu guccaggucu accaaaaaauc ucaauauuuc agauaaucac aauacacccc | 5100 |
| uuaccuggga aagggcuguu auaaucuuuc acaggggaca ggauggguucc cuugaugaag | 5160 |
| aaguugauau gccuuuuccc aacuccagaa agugacaagc ucacagaccu uugaacuaga | 5220 |
| guuuagcugg aaaaguaugu uagugcaaau ugucacagga cagcccuucu uuccacagaa | 5280 |
| gcuccaggua gagggugugu aaguagauag gccauggggca cugugggguag acacacauga | 5340 |
| aguccaagca uuuagaugua uagguugaug gugguauguu uucaggcuag auguauguac | 5400 |
| uucaugcugu cuacacuaag agagaauag agacacacug aagaagcacc aaucaugaau | 5460 |
| uaguuuuaua ugcuucuguu uuauaauuuu gugaagcaaa auuuuucuc uaggaaauau | 5520 |
| uuauuuuaau aauguuucaa acauauauaa caaugcugua uuuuaaaga augauuauga | 5580 |
| auuacauuug uauaaaauaa uuuuuauauu ugaaauauug acuuuuuaug gcacuaguau | 5640 |
| uucuaugaaa uauuauguua aaacuggac aggggagaac cuaggggugau auuaaccagg | 5700 |
| ggccaugaau caccuuuugg ucuggaggga agccuuggg cugaugcagu guugccac | 5760 |
| agcuguauga uucccagcca gcacagccuc uuagaugcag uucugaagaa gauggguacca | 5820 |
| ccagucugac uguuuccauc aagggguacac ugccuucuca acuccaaaacu gacucuuaag | 5880 |
| aagacugcau uauauuuauu acuguaagaa aauaucacuu gucaauaaaa uccauacauu | 5940 |
| ugugugaaa | 5949 |

<210> SEQ ID NO 13
<211> LENGTH: 25

```
<212> TYPE: RNA
<213> ORGANISM: Artificial Sequence
<220> FEATURE:
<223> OTHER INFORMATION: Antisense Oligonucleotide

<400> SEQUENCE: 13
cuugugaaac uuacugauua ucagg                                             25

<210> SEQ ID NO 14
<211> LENGTH: 25
<212> TYPE: RNA
<213> ORGANISM: Artificial Sequence
<220> FEATURE:
<223> OTHER INFORMATION: Antisense Oligonucleotide

<400> SEQUENCE: 14
ccucuuaccu caguuacaau uuaua                                             25

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agcatttgct gattgcacag                                                   20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gaaagagctt caccctgtcg                                                   20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
aatgctggaa tgccaacaat t                                                 21

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ggctcctctc gttcagcagt                                                   20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
```

```
gggccaaatg actgtcaaag                                              20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gcaacagatg gaagactctt gt                                           22

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gccatattag agaacatttc cttctca                                      27

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
accttgtggt ctccagaaat caa                                          23

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
ggttctttgt ggtgttttta tct                                          23

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gcaataaaca aaatacagga tttc                                         24

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
aaacttggag atgtcctctt c                                            21

<210> SEQ ID NO 26
<211> LENGTH: 23
<212> TYPE: DNA
<213> ORGANISM: Artificial Sequence
```

```
<220> FEATURE:
<223> OTHER INFORMATION: Primer

<400> SEQUENCE: 26
tgctaaagaa attcttgctc gtt                                          23

<210> SEQ ID NO 27
<211> LENGTH: 335
<212> TYPE: DNA
<213> ORGANISM: Homo sapiens

<400> SEQUENCE: 27
attgaaaata tctgacaaac tcatctttta tttttgatgt gtgtgtgtgt gtgtgtgtgt    60 tttttaaca gggatttggg gaattatttg agaaagcaaa acaaaacaat aacaatagaa   120
aaacttctaa tggtgatgac agcctcttct tcagtaattt ctcacttctt ggtactcctg   180
tcctgaaaga tattaatttc aagatagaaa gaggacagtt gttggcggtt gctggatcca   240
ctggagcagg caaggtagtt cttttgttct tcactattaa gaacttaatt tggtgtccat   300
gtctcttttt ttttctagtt tgtagtgctg gaagg                              335

<210> SEQ ID NO 28
<211> LENGTH: 452
<212> TYPE: DNA
<213> ORGANISM: Homo sapiens

<400> SEQUENCE: 28
ctaaatttca gttgacttgt catcttgatt tctggagacc acaaggtaat gaaaaataat    60
tacaagagtc ttccatctgt tgcagtatta aaatggtgag taagacaccc tgactaaatt   120
tcagttgact tgtcatcttg atttctggag accacaaggt aatgaaaaat aattacaaga   180
gtcttccatc tgttgcagta ttaaaatggt gagtaagaca ccctgactaa atttcagttg   240
acttgtcatc ttgatttctg gagaccacaa ggtaatgaaa aataattaca agagtcttcc   300
atctgttgca gtattaaaat ggtgagtaag acacccctgac taaatttcag ttgacttgtc   360
atcttgattt ctggagacca caaggtaatg aaaaataatt acaagagtct tccatctgtt   420
gcagtattaa aatggtgagt aagacaccct ga                                  452
```